United States Patent
Starc

(10) Patent No.: US 7,983,742 B2
(45) Date of Patent: Jul. 19, 2011

(54) MULTI-CHANNEL SYSTEM FOR BEAT TO BEAT QT INTERVAL VARIABILITY

(76) Inventor: Vito Starc, Ljubljana (SI)

(*) Notice: Subject to any disclaimer, the term of this patent is extended or adjusted under 35 U.S.C. 154(b) by 1099 days.

(21) Appl. No.: 11/678,839

(22) Filed: Feb. 26, 2007

(65) Prior Publication Data

US 2007/0203418 A1    Aug. 30, 2007

Related U.S. Application Data

(60) Provisional application No. 60/767,030, filed on Feb. 27, 2006.

(51) Int. Cl.
*A61B 5/04* (2006.01)

(52) U.S. Cl. ......... 600/509; 600/508; 600/515; 600/516; 600/521; 607/9; 607/17; 607/25; 128/920

(58) Field of Classification Search .......... 600/508–509, 600/515–516, 521; 607/1–2, 9, 17, 25; 128/920
See application file for complete search history.

(56) References Cited

U.S. PATENT DOCUMENTS

| | | | |
|---|---|---|---|
| 5,217,021 A * | 6/1993 | Steinhaus et al. ............ | 600/515 |
| 5,348,020 A * | 9/1994 | Hutson ......................... | 600/509 |
| 5,419,338 A | 5/1995 | Sarma et al. | |
| 5,560,368 A | 10/1996 | Berger | |
| 6,238,350 B1 | 5/2001 | Neilson | |
| 6,384,039 B1 | 5/2002 | Fossa | |
| 6,438,409 B1 | 8/2002 | Malik et al. | |
| 6,847,840 B2 | 1/2005 | DePasquale et al. | |
| 7,113,820 B2 | 9/2006 | Schlegel et al. | |
| 2002/0138012 A1 | 9/2002 | Hodges et al. | |
| 2003/0208129 A1 | 11/2003 | Beker et al. | |

OTHER PUBLICATIONS

Vrtovec et al., Beat-to_beat QT interval variability in coronary patients, J. Electrocardiol. 2000; 33(2):119-25.
Vrtovec et al., Coronary artery disease alters ventricular repolarization dynamics in type 2 diabetes. Pacing Clin Electrophysiol. 2005; 28 Suppl. 1:S178-81.
Johansson et al., Elevated temporal QT variability index in patients with chronic renal failure. Clin Sci (Lond.) 2004; 107(6):583-8.
Murabayashi, et al., Beat-to-beat QT interval variability associated with acute myocardial ischemia. J. Electrocardiol. 2002;35(1):19-25.

(Continued)

*Primary Examiner* — Carl H Layno
*Assistant Examiner* — Deborah Malamud
(74) *Attorney, Agent, or Firm* — Law Office of Tim Cook P.C.

(57) ABSTRACT

A PC-based ECG software program that in real time, acquires, analyzes and displays QTV and PQ interval variability (PQV) in each of the independent channels that constitute the 12-lead conventional and/or Frank X, Y, Z lead ECG. The system also analyzes and displays the QTV and PQV from QT and PQ interval signals that are derived from multiple channels and from singular value decomposition such that the effect of noise and other artifacts on the QTV and PQV results are substantially reduced compared to existing single-channel methods. Moreover, this invention also provides certain new parameters of T-wave (and QRS and P-wave) morphology, that in initial studies have improved clinical diagnostic utility and/or reproducibility and reliability compared to known existing parameters of T-wave morphology. Finally, it also provides a method for determining the beat-to-beat variability these T, QRS and P-wave morphologic parameters.

8 Claims, 14 Drawing Sheets

OTHER PUBLICATIONS

Nahshoni et al., Complexity of the dynamic QT variability and RR variability in patients with acute anterior wall myocardial infarction. J. Electrocardio. 2004;37(3):173-9.

Piccirillo et al., QT-interval variability and autonomic control in hypertensive subjects with left ventricular hypertrophy. Clin Sci. (Lond.) 2002;102(3):363-71.

Atiga et al., Temporal repolarization lability in hypertrophic cardiomyopathy caused by beta-myosin heavy-chain gene mutations. Circulations 2000;101(110:1237-42.

Berger et al., Beat-to-beat QT interval variability: novel evidence for repolarization lability in ischemic and nonischemic dilated cardiomyopathy. Circulation 1997;96(5):1557-65.

Berger, QT variability. J. Electrocardiol. 2003;36 Suppl:83-7.

Atiga et al., Beat-to-beat repolarization lability identifies patients at risk for sudden cardiac death. J. Cardiovasc Electrophysiol 1998;9(9):899-908.

Thomsen et al., Increased short-term variability of repolarization predicts e-sotalol-induced torsades de pointes in dogs. Circulation 2004;110(16):2453-9.

Gao et al., Reproducibility of methods for assessing baroreflex sensitivity and temporal QT variability in end-stage renal disease and healthy subjects. Clin. Auton. Res. 2005;15(1):21-8.

Govreen-Segal et al., Real-time PC-based system for dynamic beat-to-beat QT-RR analysis. Comput Biomed Res. 1999;32(4):336-54.

Forester et al., Variability of R-R, P wave-to-R wave, and R wave-to-T wave intervals. Am J. Physiol. 1997;273(6Pt2):H2857-60.

Shouldice et al., Modulating effect of respiration on atrioventricular conduction time assessed using PR interval variation. Med Biol Eng Comput. 2002;40(6):609-17.

Arnol et al., Atrioventricular conduction variability in coronary patients. J Electrocaridol. 2003;36(4): 311-9.

Malik et al., Measurement, interpretation and clinical potential of QT dispersion. J Am Coll Cardiol. 2000;36(6):1749-66.

Heart rate variability. Standards of measurement, physiological interpretation, and clinical use. Task Force of the European Society of Cardiology and the North American Society of Pacing and Electrophysiology. Eur. Heart J. 1996;17(3):354-81.

Malik et al., QT dispersion does not represent electrocardiographic interlead heterogeneity of ventricular repolarization. J Cardiovasc Electrophysiol. 2000;11(8):835-43.

Press, Numerical recipes in C: the art of scientific computing. 2nd ed. Cambridge; New York: Cambridge University Press; 1992:59-70.

Zabel et al., Analysis of T-wave morphology from the 12-lead electrocardiogram for prediction of long-term prognosis in male US veterans. Circulation 2002;105(9):1066-70.

Okin et al., Repolarization abnormality for prediction of all-cause and cardiovascular mortality in American Indians: the Strong Heart Study. J Cardiovasc Electrophysiol. 2005;16:1-7.

Batdorf et al.,. The Effect of Signal Averaging on the Reproducibility and Reliability of Measures of T-wave Morphology. J Electrocardiol. 2006 (in press).

Bernardi et al., Effect of rosary prayer and yoga mantras on autonomic cardiovascular rhythms: comparative study. Bmj. 2001;323(7327):1446-9.

Malik Problems of heart rate correction in assessment of drug-induced QT interval prolongation. J Cardiovasc Electrophysiol. 2001;12(4):411-20.

* cited by examiner

MULTI-CHANNEL SYSTEM FOR BEAT TO BEAT QT INTERVAL VARIABILITY

This application claims the benefit of U.S. Provisional Patent Application Ser. No. 60/767,030 filed Feb. 27, 2006.

FIELD OF THE INVENTION

The present invention relates generally to the field of electrocardiography, and more particularly to a processing system and method to analyze and display electrocardiographic signals to indicate: 1) the variability of the QT and PQ intervals from one beat to the next; and 2) the decomposed morphology of the T, P and QRS waves and the variability of this morphology from one beat to the next.

BACKGROUND OF THE INVENTION

The measurement of beat-to-beat QT interval variability (QTV) shows clinical promise for identifying several types of cardiac pathology, including coronary artery disease, acute myocardial ischemia and infarction, left ventricular hypertrophy, and various types of cardiomyopathy. Importantly, in patients referred for electrophysiologic studies and in animals who receive drugs that prolong the QT interval, increased repolarization lability as reflected by increased beat-to-beat QTV is strongly predictive of future arrhythmic events. As such, several researchers have recently developed software programs to quantify QTV.

However, there are a number of limitations associated with these existing software programs. First, most if not all such programs require the operator to actively perform certain functions, for example that the operator manually choose the onset and offset of an initial QT interval template. This step of human intervention is both time consuming and labor intensive, and affects the reproducibility of the result. Second, most existing programs also allow for QTV analyses in only one single channel at a time (i.e., usually in limb lead II or limb lead I), and not in multiple channels simultaneously. This can lead to spuriously high QTV values, particularly when the T wave in the channel being studied is small, noisy or otherwise poorly defined. Third, no known existing programs for QTV analyses perform in real time, only offline, with the exception of one real-time program that is focused on dynamic QT vs. RR plots and which in any case has the other limitations noted above. A lack of real-time capability necessarily entails that any acute or subacute change in QTV, as might occur for example during myocardial ischemia or the treatment thereof, cannot be readily observed or acted upon. Similar limitations also apply to all existing programs that attempt to measure PQ interval variability (PQV).

Schlegel et al., in U.S. Pat. No. 7,113,820, assigned to the same assignee as the present invention, provided a real-time ECG analysis system. In the system of the '820 patent, cardiac electrical data were received from a patient, manipulated to determine various useful aspects of the ECG signal, and displayed in real time in a useful form on a computer screen or monitor. The monitor displayed the high frequency data from the QRS complex in units of microvolts, juxtaposed with a display of conventional ECG data in units of millivolts or microvolts. The high frequency data were analyzed for their root mean square (RMS) voltage values and the discrete RMS values and related parameters were displayed in real time. The high frequency data from the QRS complex were analyzed with imbedded algorithms to determine the presence or absence of reduced amplitude zones, referred to as "RAZs". RAZs were displayed as "go, no-go" signals on the computer monitor. The RMS and related values of the high frequency components were displayed as time varying signals, and the presence or absence of RAZs could be similarly displayed over time. This system has proved to be very successful, but did not provide the means to analyze QT or PQ variability, as in the systems referred to above.

On the other hand, in U.S. Pat. No. 5,560,368, Berger taught a method for semi-automated, offline QT variability measurement. In the '368 patent, Berger suggested a method for analyzing electrocardiograph signals that involved: sensing fluctuations in voltage resulting from electrical activity of a heart as signals having an analog value; converting such signals having an analog value to digital values corresponding substantially to the analog value of the signals; recording the digital values in a record; analyzing the digital values of the record offline by: identifying a time of each R wave of a heartbeat; manually defining a template QT interval for a heartbeat by selecting a beginning of a QRS complex and an end of a T wave for the heartbeat; determining an alteration value selected from the group consisting of an elongation of a heartbeat in time and a compression of a heartbeat in time as an error function for the heartbeat; performing a binary search to determine a minimal value for the error function; and assessing changes in QT interval for each heartbeat using the entire T wave. However, the Berger et al. method suffered from the same drawbacks as other QTV systems as described above.

In addition, in U.S. Pat. No. 6,438,409, Malik et al taught a method for offline analysis of T-wave morphology (TWM) that focused on the percentage contribution of the strictly "non-dipolar" components of the T-wave to the total energy of the T-wave as determined by utilizing singular value decomposition (SVD) and calculating the so-called "relative T-wave residuum", TWR. Although Malik et al's TWR parameter may help to supplement other pre-existing measures of TWM, such as the so-called "complexity ratio" earlier introduced by Priori et al., the TWM parameters of Malik et al. are subject to certain critical limitations that adversely impact their clinical utility. For example, the TWR parameter is hampered by its poor reproducibility, and, especially when signal averaging is not performed, TWR may often in fact represent more noise than signal.

Thus, there remains a need for a computer based system that allows for: 1) fully automatic and real-time monitoring of a plurality of indices of QTV and PQV for each of a plurality of channels of an electrocardiogram; and for 2) improved parameters of TWM (and also of P-wave and QRS-wave morphology) that have improved clinical utility. The system should also provide automatically measured parameters which are more reproducible and reliable than all existing measures of QTV, PQV and TWM in terms of accurately predicting the presence of underlying cardiac pathology. The system should be adaptable to standard, in-place systems and require no operator interference with the selection of various criteria of the ECG waveforms. The present invention is directed to solving these and other drawbacks in the art.

SUMMARY OF THE INVENTION

To address these limitations, the present invention provides a PC-based software program that allows for the automated and real-time monitoring of multiple indices of QTV and PQV, not only in each of the independent channels that constitute the standard 12-lead or Frank-lead ECG, but also in certain related signals derived from singular value decomposition (SVD) that help to reduce the overall effects of noise. The development of this invention was, in part, based on the assumption that automatically constructed templates are more reproducible than manually constructed templates, and also better meet the demand for rapid and regular updating as required for the continuous and real-time monitoring of changes in QTV, PQV and TWM. It was also assumed that QT and PQ interval data derived from multiple leads not only provide more information than similar data derived from a single lead, but also, with proper statistical treatment, help to reduce the effects of noise.

The method of the present invention analyzes ECG waveforms first by automatically identifying individual beats and particular waves, then by automatically forming templates for each individual wave (P, QRS and T) in each individual lead, then by constructing time series for the RR, QT and PQ intervals, and finally by: 1) statistically describing the beat-to-beat variability of the last "N" recorded QT and PQ intervals within all standard leads and within multiple derived (e.g., decomposed) leads, and by 2) characterizing novel parameters of T, P, and QRS-wave morphology, as well as the beat-to-beat variability of these parameters. The automatic detection of intervals and the automatic formation of signal-averaged templates both serve to eliminate any dependencies on the individual operator, while the automatic formation of templates also provides quality control for consistency in the determination of the QT and PQ intervals and of the T, P, and QRS waves. The use of data from multiple leads (including from SVD) rather than from a single lead also results in a more accurate determination of QTV and PQV by preventing the inadvertent analysis of noise and by eliminating important artifacts such as jitter in the detected QRS-wave fiducial points. Thus, the present invention provides a method of analyzing ECG signals including analyzing the digital values of the record in real-time by identifying a time of each R wave of a heartbeat. The method also includes defining individual signal averaged templates for the T wave and the QRS wave for a series of heartbeats by segmenting each heartbeat of the series of heartbeats at the beginning and the end of the QRS wave and the T wave, and using the defined individual templates to determine alteration values for individual T waves and QRS waves of an individual heartbeat. These alteration values comprise shifts in time of the T wave and QRS wave as error functions for the heartbeat. Finally, the method includes assessing changes in QT interval for each heartbeat using the T wave template, the QRS wave template, and the series of heartbeats. The method of this invention applies equally to defining individual signal averaged templates for the P wave and the QRS wave.

These and other features and advantages of the present invention will be apparent to those of skill in the art from a review of the following detailed description along with the accompanying drawing figures.

DETAILED DESCRIPTION OF PREFERRED EMBODIMENTS

The present invention uses a software program to analyze multilead ECG signals of a conventional ECG in real-time or stored for subsequent analysis. One advantage of the system of this invention resides in the fact that it analyzes a plurality of received ECG signals simultaneously and automatically without the need for an operator to select and define trigger points on or near the QRS, T, or P waves. The system automatically calculates various parameters from the received ECG waveforms related to the electrical depolarization and especially repolarization of the cardiac chambers that helps to differentiate diseased hearts from non-diseased hearts. The system also uses certain signal analysis techniques to reduce the effects of noise, jitter, and other deleterious effects which presently plague known systems.

To accomplish these goals, the system measures and analyzes the voltage-time data for any three or more channels of data that contribute to the conventional 12-lead or Frank-lead ECG including, as desired, to any alternative lead set system that might complement the standard limb or $V_1$-$V_6$ precordial leads, such as a $CR_1$-$CR_6$ precordial lead set, a $V_{1R}$-$V_{6R}$ precordial set, or any lead set shifted to higher intercostal spaces for better definition of electrical events within the PQ interval, or to more lateral areas for better definition of certain myocardial infarctions or ischemia, etc. The voltage-time data are fed into a computer that is programmed with the program of the present invention.

The computer system then provides as outputs: 1) the QT and PQ signals, consisting of a sequence of QT and PQ intervals belonging to each beat; 2) signal averaged templates for each of the waves of the ECG, including a T-wave template from which the most clinically useful TWM parameters are derived in real time; and 3) all QTV and PQV related parameters. The software process consists of two principal parts that follow each other sequentially during execution of the program, in order to first construct template signals and then to process individual beats from the ECG leads.

Figure 1:
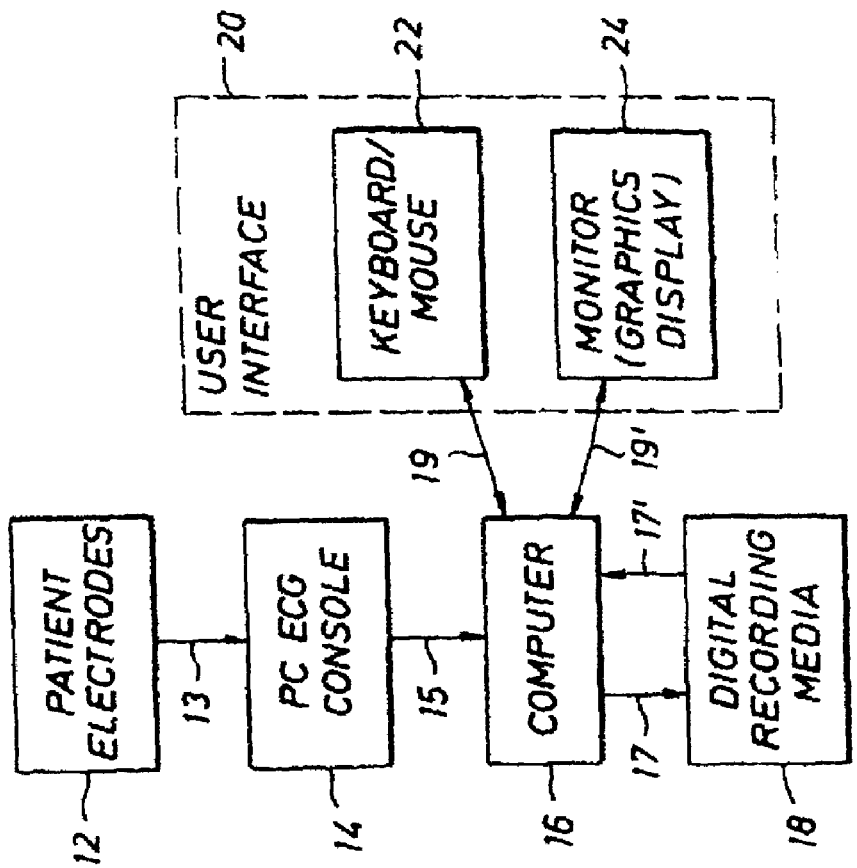
FIG. 1 is a schematic diagram of the overall system of this invention.

FIG. 1 shows a simplified, functional, block diagram of a real-time multichannel QTV electrocardiograph 10 constructed in accordance with the present invention. The invention monitors the cardiac function of a patient with a plurality of patient electrodes 12. The electrodes provide measurements of cardiac electrical function at various contact points on the skin of a patient in the conventional manner. For example, in the conventional 12-lead configuration, 10 electrodes placed upon the skin of the patient in the conventional configuration result in eight channels of incoming data. These eight channels are in turn translated into twelve leads of data on the patient monitor inasmuch as data for one of the bipolar limb leads and for all of the augmented unipolar limb leads can be derived if data for any two of the bipolar limb leads are already known. The analog measurements are coupled to a console 14 by way of a communications channel such as for example a cable 13.

The console 14 conditions and digitizes the analog signal and provides the digitized signal to a computer 16 by way of a communications channel 15, which may preferably be a conventional cable or a wireless communication channel by radio frequency wave. In a preferred embodiment, various functions of the signal acquisition and process are carried on by multiple processors. The computer 16 is programmed to display the ECG signal in real time, although the ECG signal may also be stored on a digital recording medium 18 over a communications channel 17 for later display over a communications channel 17'. The computer 16 is also programmed to automatically detect QT and other intervals, on a beat-to-beat basis, and to compare those detected intervals to continuously updated templates, also developed by the computer.

The computer 16 is coupled to a user interface 20 which preferably includes communications devices 22 such as a mouse, keyboard, and/or touch screen. The user interface further includes a monitor 24 for user controllable graphic display of the ECG and various aspects of the signal, a feature of the present invention. The computer 16 is coupled to the interface 20 by way of bidirectional communications channels 19 and 19', for example.

Figure 2:
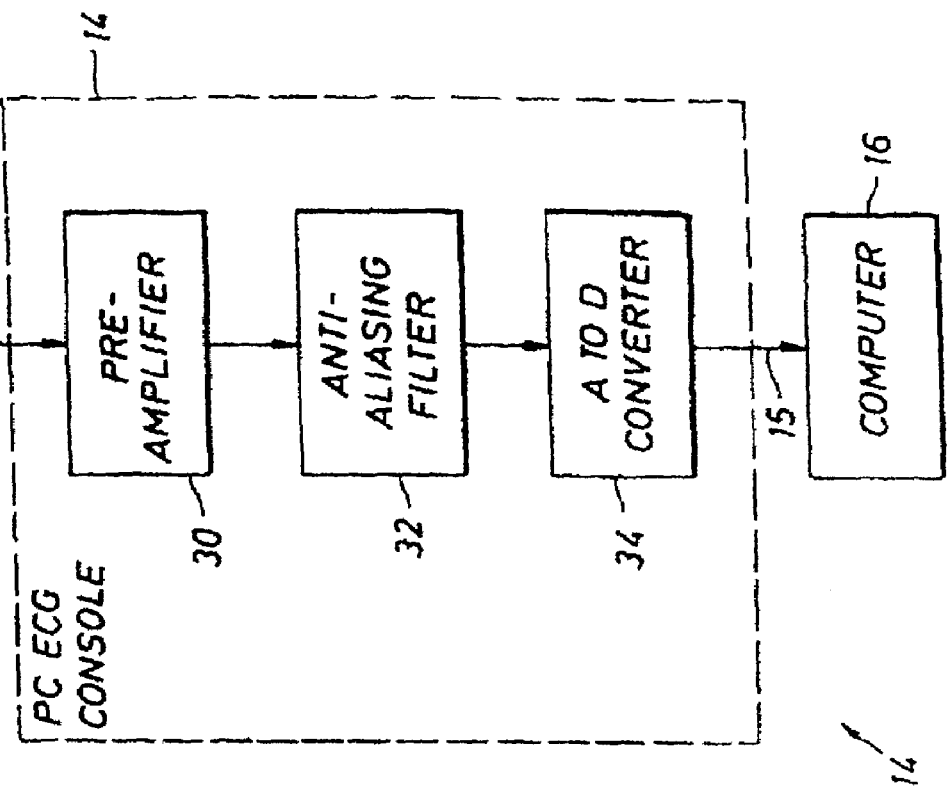
FIG. 2 is a schematic diagram of a detail of FIG. 1.

FIG. 2 depicts the structure of the console 14 in greater detail. As previously described, the patient is wired with a set of electrodes 12, which provide a set of analog electrical signals to the console 14, where they are received by a preamplifier 30 to boost the amplitude of the weak ECG signals. The amplified signals are then fed to an anti-aliasing filter 32. The filtered signals are fed to an analog to digital converter 34, where the signals are digitized at at least the Nyquist rate, preferably 1,000 Hz or greater, to retain all of the information contained in the analog signals. The sampled/digitized signals are then sent to the computer 16 by an appropriate medium 15.

To properly condition the analog signals for processing and subsequent analysis, the low-pass filtering characteristic of the amplifier 30 should be around 100 Hz, and the sampling rate of the analog to digital conversion should not be smaller than 100 samples/sec. In case of higher sampling rate (preferably 1000 samples/sec) and higher low-pass cutoff, the signal should be filtered digitally.

Symbols and Definitions

In the detailed description below, the following symbols and definitions will be used:
- $i$—beat number
- $j$—sample number
- $k$—ECG lead (e.g., standard leads I, II, III, aVF, aVR, aVL, precordial leads $V_1, V_2, V_3, V_4, V_5,$ and $V_6$, Frank leads X, Y and Z, decomposed signals $SVD_1, \ldots SVD_8$, and the radius vector amplitude signal (RVA))
- $l$—template number (or the template's generation)
- $M_0(l), M_1(l)$,—beat numbers of the first and last beat in the sequence used for construction of the l-th template
- $n$—number of beats in the template or in the beat waveform
- $W$—wave index for the wave component (for P, QRS and T waves)
- $n_1(k,W)$ and $n_2(k,W)$—matching window borders (the lowest and the highest values) for the k-th lead and W-th wave
- $X_{i,k,W}$—beat waveform of the i-th beat, k-th lead and specifying the matching window for the W-th wave component to be analyzed (Since in the analysis, the beat signal is split into the particular waves, it also denotes the corresponding wave of the i-th signal, i.e. the QRS, P or T wave)
- $\phi_{l,k,W}$—template waveform of the l-th generation, k-th lead and specifying the matching window for the W-th wave component
- $w_n$—eigenvalue of the n-th eigenvector (principal signal)
- $a_{i,k,W}$—delay (or the time shift) of the W-th wave of the i-th beat with respect to the appropriate template
- $A_{k,W}$—the mean value of $a_{i,k,W}$ from beats of the l-th generation, used to define the range of delays for accepting a given delay into the appropriate averaging bin
- $\Delta A_{k,W}$—width of ranges for accepting a given delay into the appropriate averaging bin
- $b_{i,k,W}$—Wave norm of the i-th beat in the interval of the W-th wave
- $b1_{l,k,W}$—Maximal value of the wave norm of the W-th wave and k-th lead for accepting a particular wave for the construction of the l-th template
- $b2_{l,k,W}$—Maximal value of the wave norm of the W-th wave and k-th lead for accepting a particular wave for the construction of the QT of PQ signal after construction of the l-th lead In a presently preferred 12-lead ECG embodiment, two processes run in parallel within the computer 16: the acquisition of data from the PC ECG console 14 and ECG wave analysis. Both processes run in a time-shared mode controlled by two separate threads on the computer 16. The first thread reads a named pipe to which raw data are provided by a server program, which results in the writing of eight channels of ECG data into a circular buffer that can contain up to the last "M" minutes of data. The ECG devices can also optionally provide the positions of the instantaneous QRS-wave fiducial points. The program then uses this information (and/or information from its own R-wave detector) to perform assessments of the amount of QRS-wave jitter that is present and to help eliminate its artifactual effects on QTV.

Figure 3:
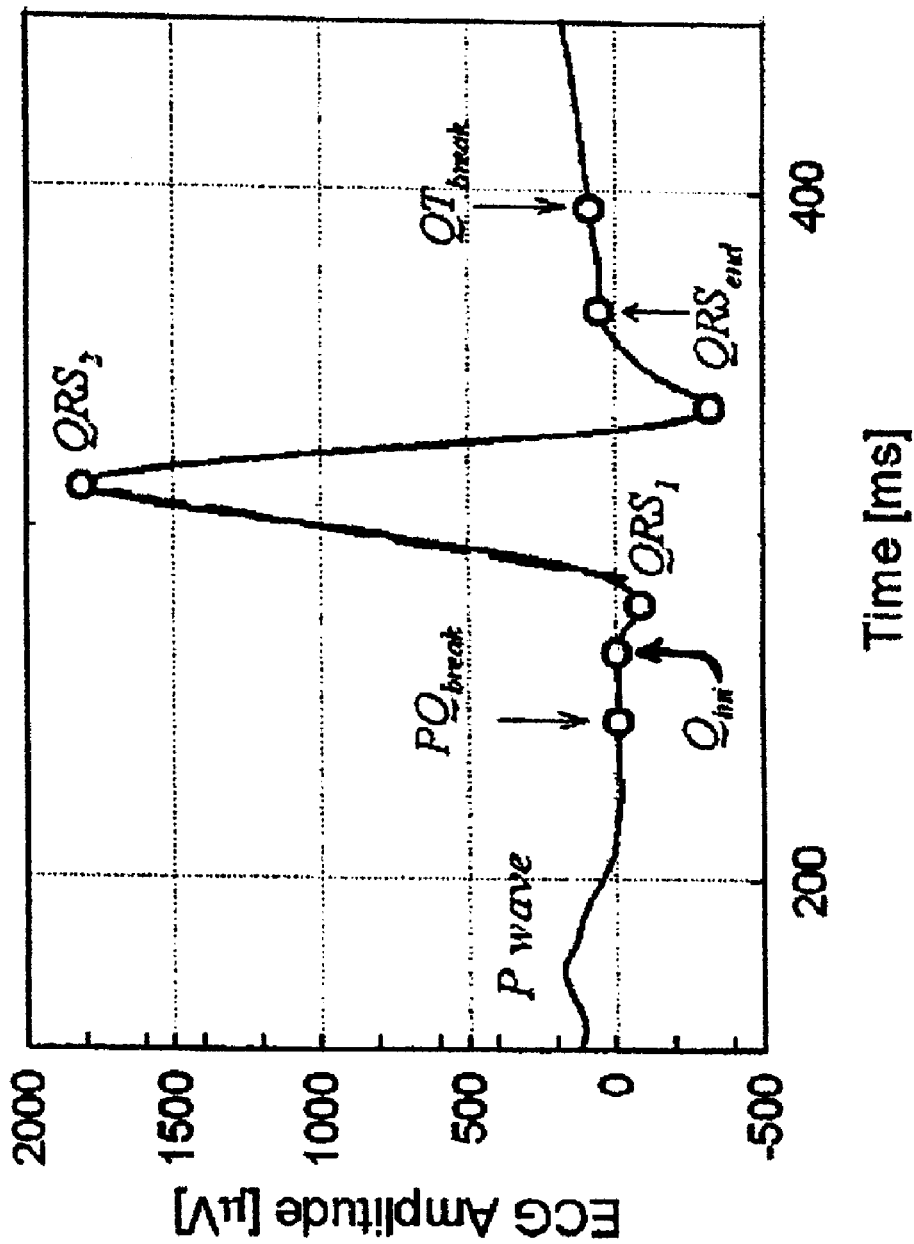
FIG. 3 is a time plot of an electrocardiograph, depicting defined characteristics of a template of the QRS complex.
Figure 4:
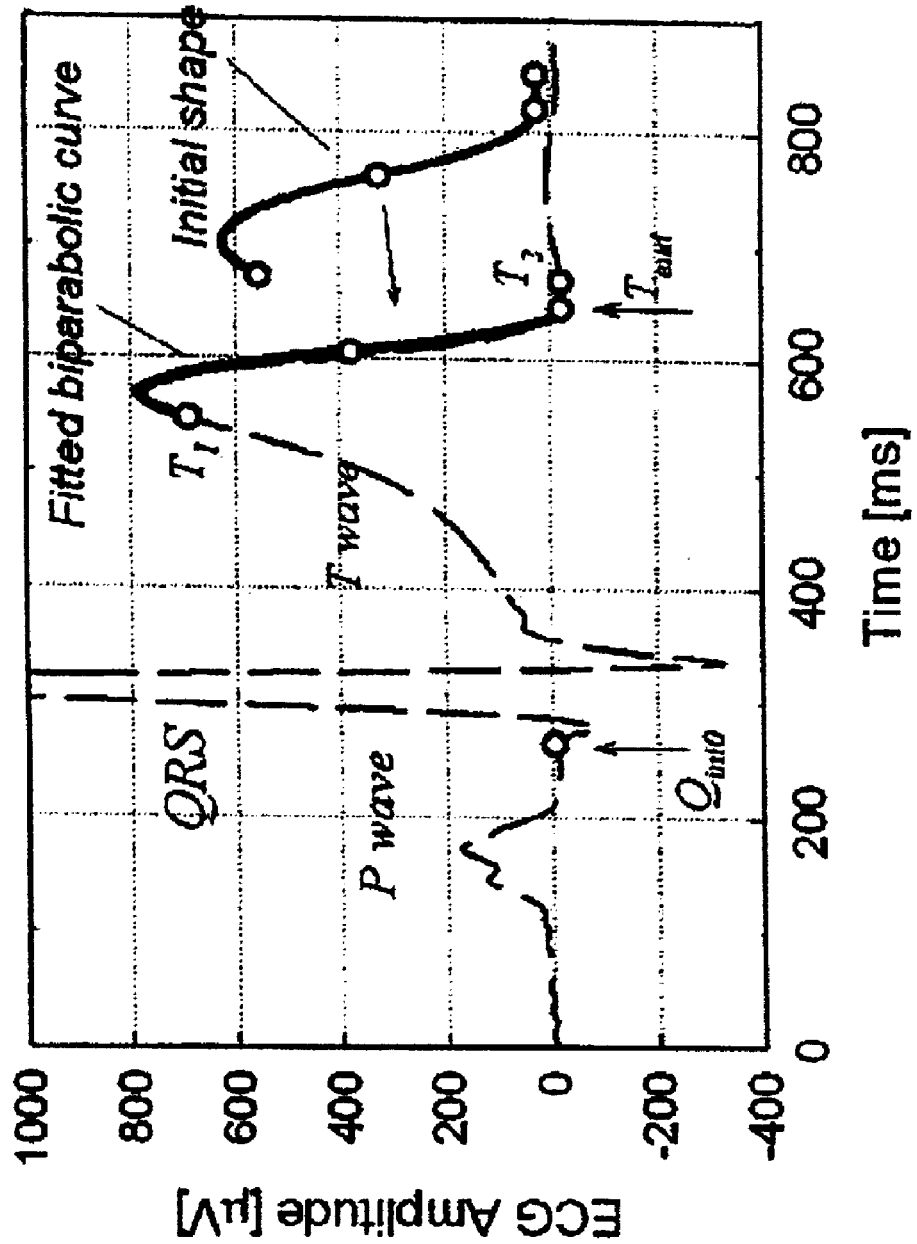
FIG. 4 is a time plot of the characteristics of a template of T wave.

Automated Formation and Update of Separate Templates for the QRS, T, and P Waves FIG. 3 depicts certain characteristics of a signal averaged template of a QRS complex. Similarly, FIG. 4 depicts characteristics of a corresponding template for the T wave. After initial global templates (described below) have been constructed, breaking points variously defined as $PQ_{break}$ (between the P wave and the QRS complex), $QT_{break}$ (between the QRS complex and the T wave), $T_{end}$ (the final point of the T wave) and $P_{ini}$ (the initial point of the P wave) are used to construct individual templates for the three principal waveforms QRS, T and P. Thus, the QRS wave template will ultimately be confined to the time interval between $PQ_{break}$ and $QT_{break}$, the T wave template to the time interval between $QT_{break}$ and $T_{end}$, and the P wave template to the time interval between $P_{ini}$ and $PQ_{break}$.

The algorithms that define the breaking points and thus the templates themselves are described separately in greater detail below. Once formed, the QRS, T and P wave templates are also updated every N beats when desired for real-time monitoring. If, for example, 60 beats is selected for N, then at the time of the first update (i.e., at the 60th overall beat), the averaging bins will be emptied and the averaging procedure will use all N (all 60 in this example) beats from the existing buffer to form its updated templates. Thereafter, for the sake of speed and real-time performance, the program will use only the last N1 beats (N1≦N) of each consecutive N-beat cycle for template updates. That is, if N1=10 and N=60 (the program's default values), then only beats 111-120 would be used for the template update at 120 beats; beats 171-180 for the template update at 180 beats, etc.

Figure 5A:
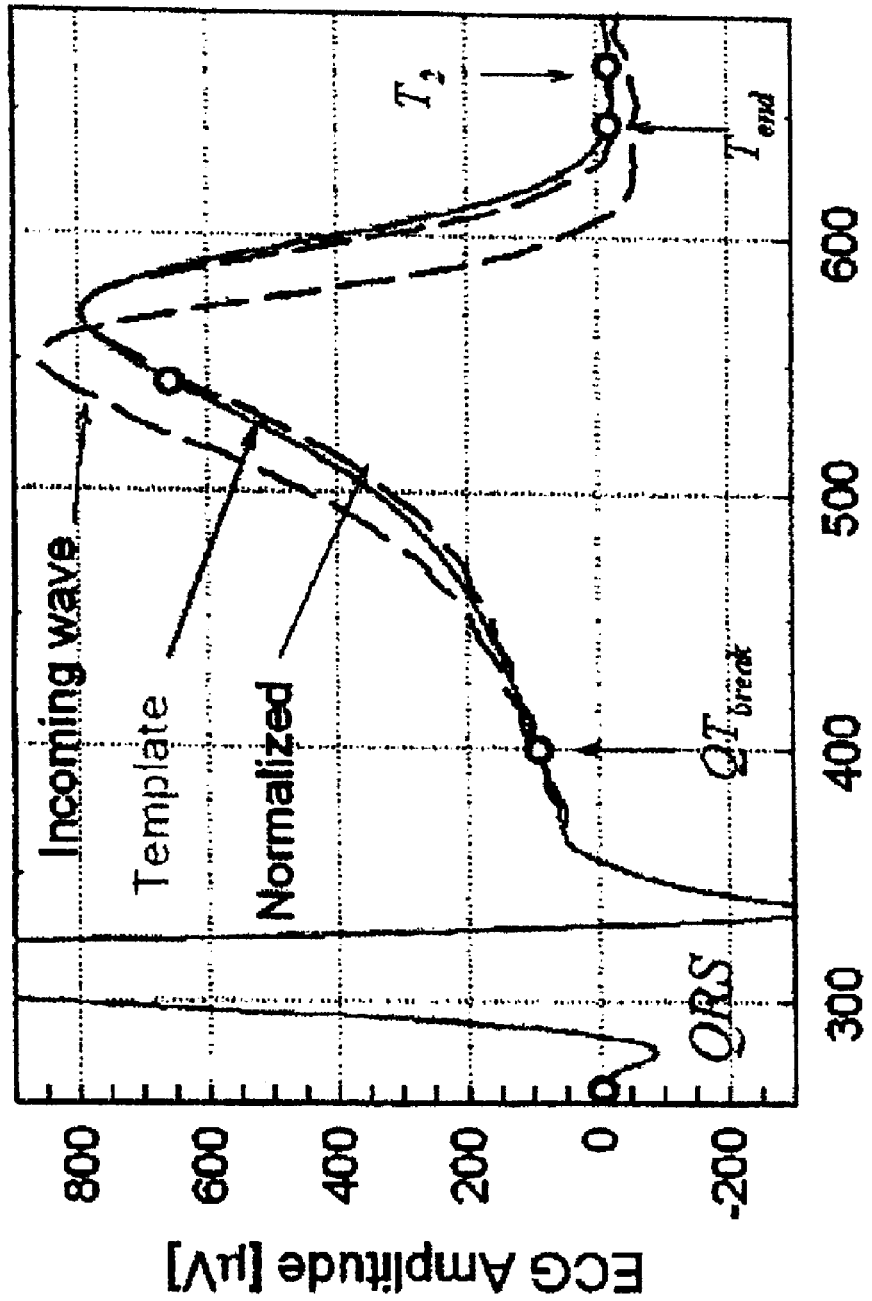
FIG. 5a is a time plot, depicting a first sub-step in shifting and normalizing a incoming, detected ECG wave to a template.
Figure 5B:
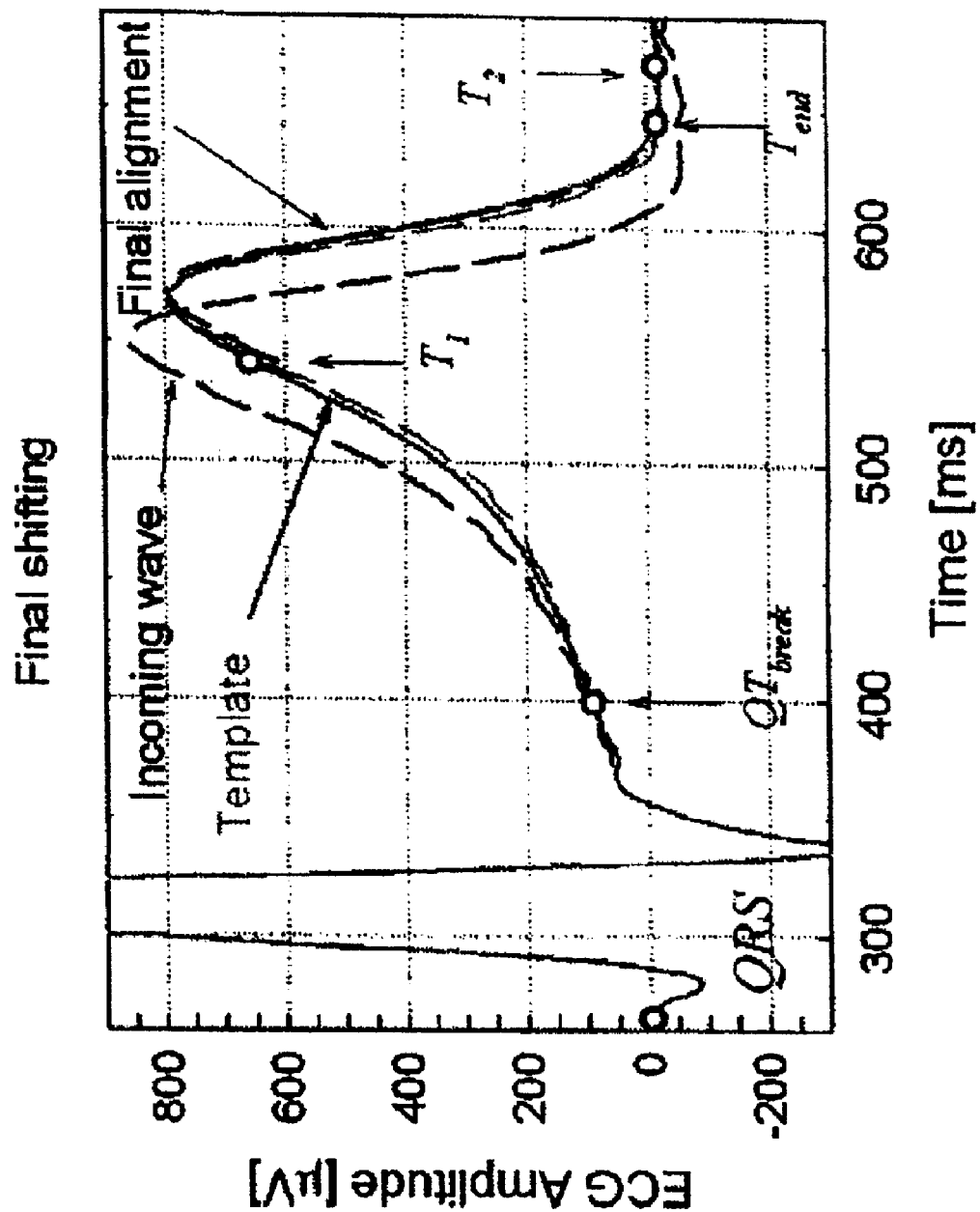
FIG. 5b is a time plot, depicting a second sub-step in shifting and normalizing an incoming, detected ECG wave to a template.

FIGS. 5*a* and 5*b* are provided at this point to depict the two-step shifting procedure of this invention, described below in greater detail.

Iterative Matching of Beat Signals with the Template

Figure 7:
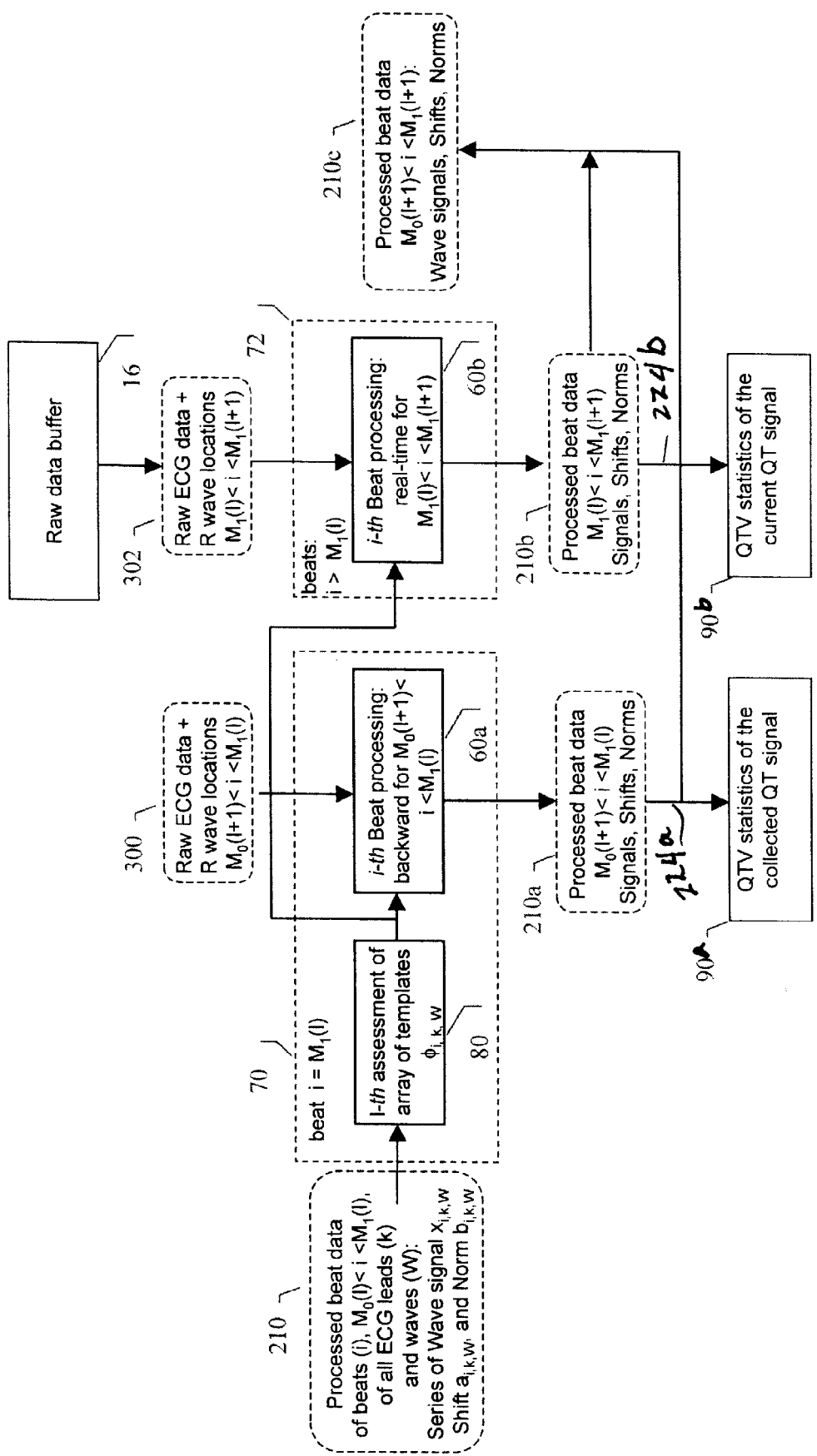
FIG. 7 is a block diagram of a process for the iterative matching of beat signals with the $l^{th}$ template.

As previously described, the present invention constructs a plurality of templates, representing portions of the ECG waveform, and compares that template to each beat on a beat-by-beat basis. FIG. 7 depicts a basic block diagram of an iterative procedure in which templates are improved with each successive construction, also providing better processed beat signals and better matching. The interchanging pattern of the template construction is provided in step 80 and beat signal processing is performed in steps 60*a* and 60*b*. After the third construction of the template, the QT interval signal is not significantly improved with further template construction, unless the beat signals that are fed into the computer change their characteristics resulting in changing the template waveform.

First, after a preselected number of beats (for example 20 beats) is received by the computer 16, an initial signal averaged template, $\phi_0$, is constructed, using beat superposition only, i.e., without previous signal processing. Next, the program processes the past 20 beats using the initial template, $\phi_0$, to obtain and align incoming beats, which are then processed in real-time until reaching the 60$^{th}$ beat. In a presently preferred embodiment, all 60 of these beats are then used to construct a new signal averaged template, $\phi_1$, which has a better signal-to-noise ratio than the initial template. Then, the program uses the newly constructed template, $\phi_1$, to process the first 60 beat signals to again obtain and align yet further newly incoming beats, which are then processed in real-time until reaching the 120$^{th}$ beat. Then, a new signal averaged template, $\phi_2$, (the third one in the sequence) is produced using the first 120 beats for its construction.

In general, as shown in FIG. 7, a new, l-th template is formed in the step 80 at the selected beat number i=$M_1$(l) in the short time interval 70 using a selected number of processed beats 210, from beat i=$M_0$(l) to beat i=$M_1$(l). Here, the template 202 (see FIG. 6, described below) represents an array of template signals $\phi_{l,k,W}$, constructed for each ECG lead (k) and for each ECG wave (W), where W is used to denote ECG waves P, QRS or T, using the processed beat data 210 including the processed wave signals $x_{i,k,W}$, the norm $b_{i,k,W}$, and the delay $a_{i,k,W}$ (212, 216 and 214, respectively, illustrated in FIG. 8) that represent the accumulated individual beats.

In the next step 60*a*, a selected number of beats from a raw data buffer 300 (from the beat i=$M_1$(l) back to the beat i=$M_0$(l+1), where $M_0$(l+1)<$M_1$(l)) are reprocessed in the rest of the time interval 70 to get a better match with the newly formed more accurate template, also providing processed beat data 210*a* with more accurate wave delays, from which a better QT signal 224*a* is recalculated to provide for QTV analysis in the step 90*a*.

With templates 202 $\phi_{l,k,W}$, incoming beats are then analyzed in real-time in step 72, to provide QT signal 224*b* in real-time for QTV statistics in the step 90*b*, and processed data 210*b* (signals, norms and delays) serve later for the construction of the next template, $\phi_{l+l,k,W}$ using the processed beat data 210*c*=210*a*+210*b*. Thus, with iterative reconstruction of the template, its shape is becoming more accurate, since it enables better procession of incoming beats.

It is not necessary to process the past beats after each new template construction, since the QT interval signal provided by the preceding beat signal processing is not expected to change considerably. Nevertheless, it is useful to analyze the past 20 beats (e.g., from beat 101 to 120) with the new template in order to link the past QT signal, which was generated by the former template, with the new QT signal generated by the new template. Slight changes in the template QT interval due to changes in the template waveforms may result in the slight offset of the newly constructed QT signal. These changes, however, can be compensated for after comparing the same part of the QT signal obtained by the two different templates.

Since the quality of matching gets better with each successive template, the repetitive construction of templates not only improves the template but also the accuracy of the beat to beat ECG interval, such as the QT interval and the PQ interval. As a result, the 'norm', an estimate of the noise of matching for each wave of a certain beat, is reduced with each new construction of the template. Usually, the template stabilizes at the third reconstruction.

The improved quality of the signal processing is due to several steps in the software program, such as 1) decomposition into principal components (the SVD method), that reduces noise and enhances the signal, and 2) selection of beats for averaging on the basis of the similarity in the QT signal value and of the beat quality, assessed by the norm. Both measures in turn improve the quality of the template that in the next matching further provides the improved processing of individual beats.

Figure 8:
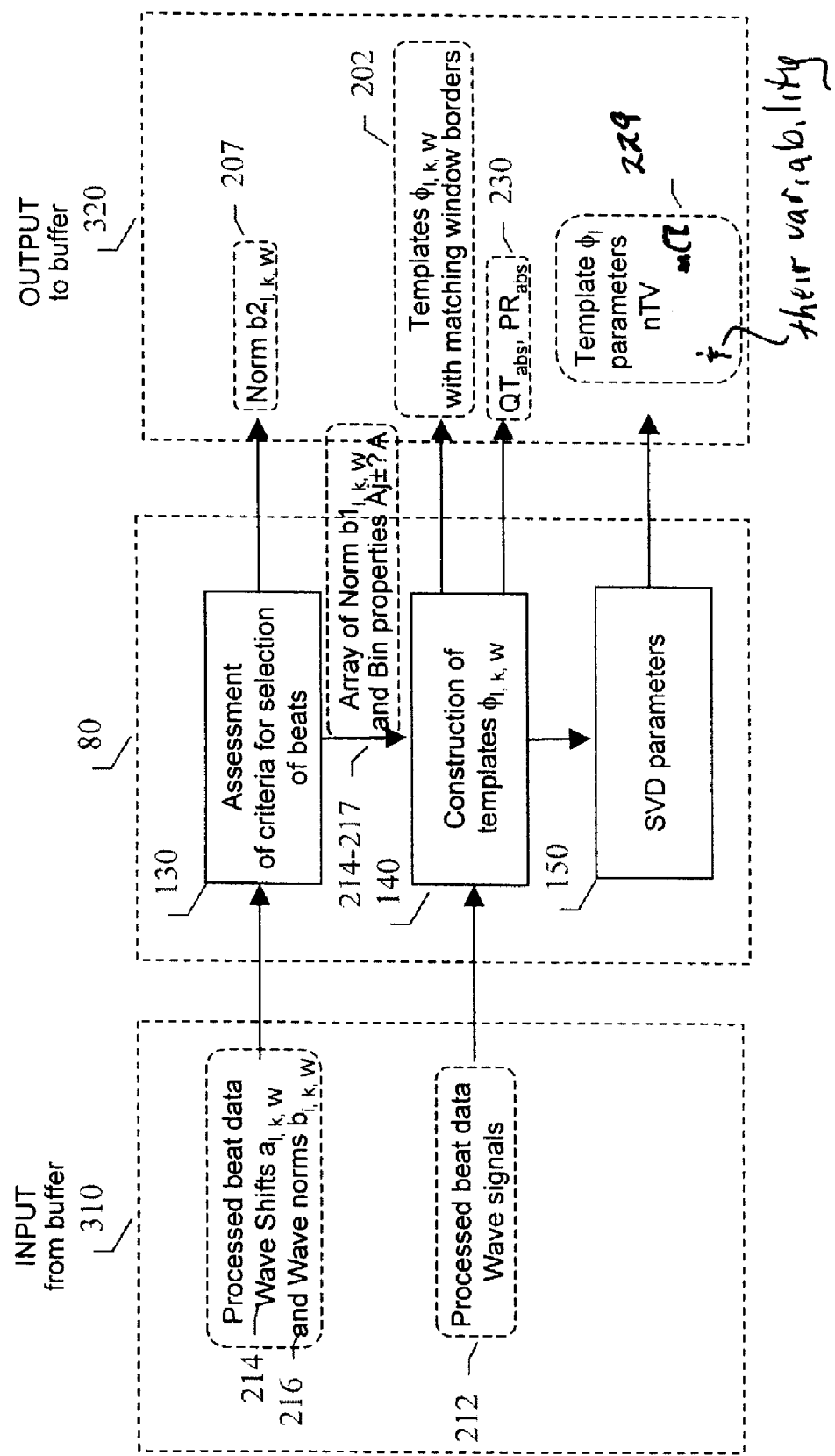
FIG. 8 is a block diagram of a process of the $l^{th}$ assessment of templates using beats from $i=M_0(l)$ to $M_1(l)$.

As shown in FIG. 8, an input buffer 310 retains processed beat data 210 consisting of the processed wave signals $x_{i,k,W}$, the norm $b_{i,k,W}$, and the time shifts $a_{i,k,W}$ (212, 216 and 214, respectively). These data are provided to the computer 16 at the beat number i=$M_1$(l) for the l-th assessment of templates in step 80, which comprises of three sub-steps. Step 130 involves the assessment of criteria for selection of beats for averaging, providing the array of norms 206 (b1$_{l,k,W}$), and the location 204 and width 205 of averaging bins ($A_{k,W}$ and $\Delta A_{k,W}$, respectively) that serves for the selection of the appropriate bin in the case of an incoming beat with the particular delay $a_{i,k,W}$. The step 130 also provides the norms 207 (b2$_{l,k,W}$) to the output buffer 320. In the Step 140, processed wave signals 212 are used for the construction of templates 202, as well as the template QT and PQ intervals 230 that are provided to the output buffer for the later construction of the QT signal. Finally, in the step 229, parameters relating to SVD-derived waveform morphology (such as the 'normalized volume' and 'modified complexity ratio' of TWM, described below) are calculated, along with the beat-to-beat variability of these parameters.

Construction of Templates for Beats i-$N_0$(l) to $N_1$(l)

Figure 11:
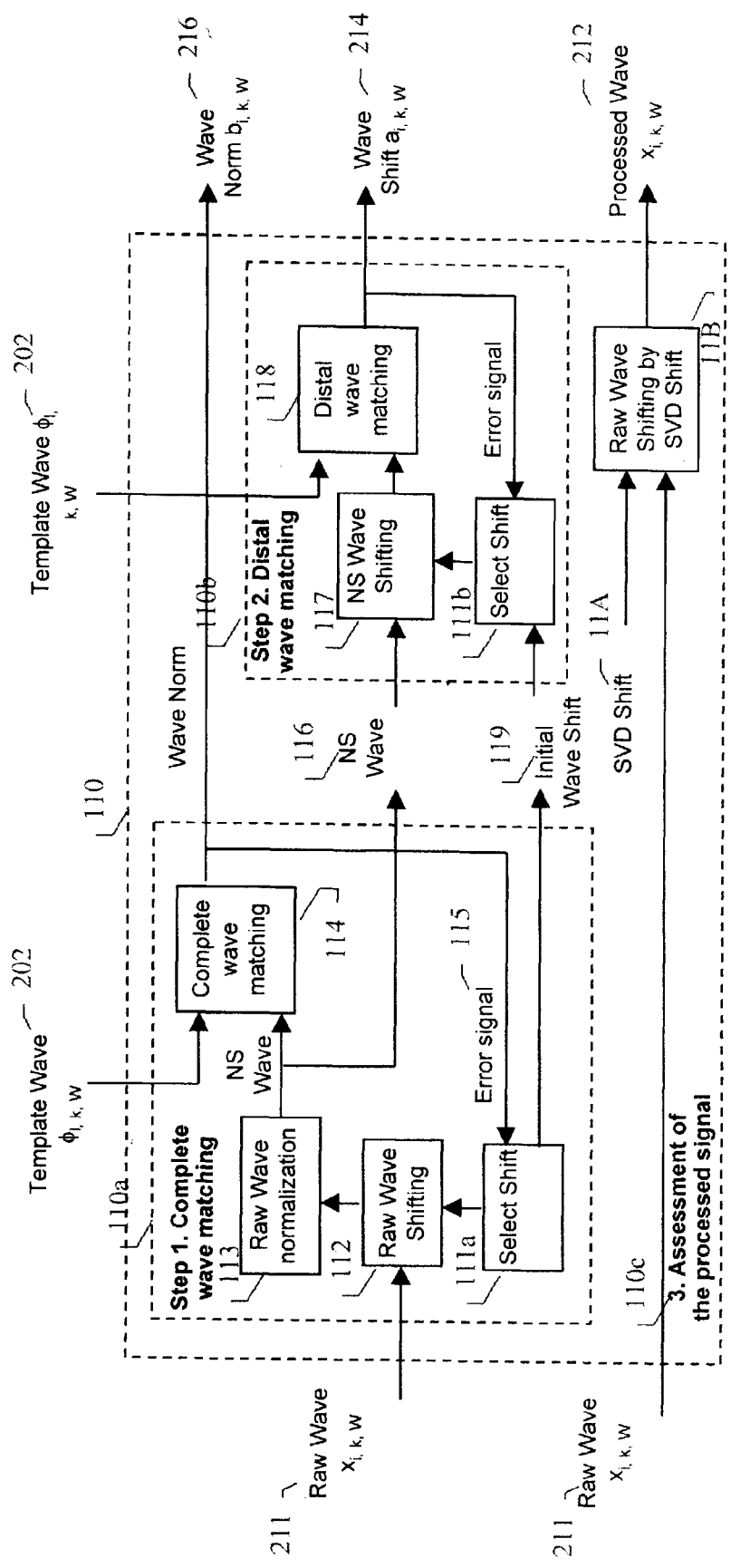
FIG. 11 is a block diagram of a method of beat signal matching with the template for each lead (k) and each wave (W) in two steps and the assessment of the processed wave signal.
Figure 12:
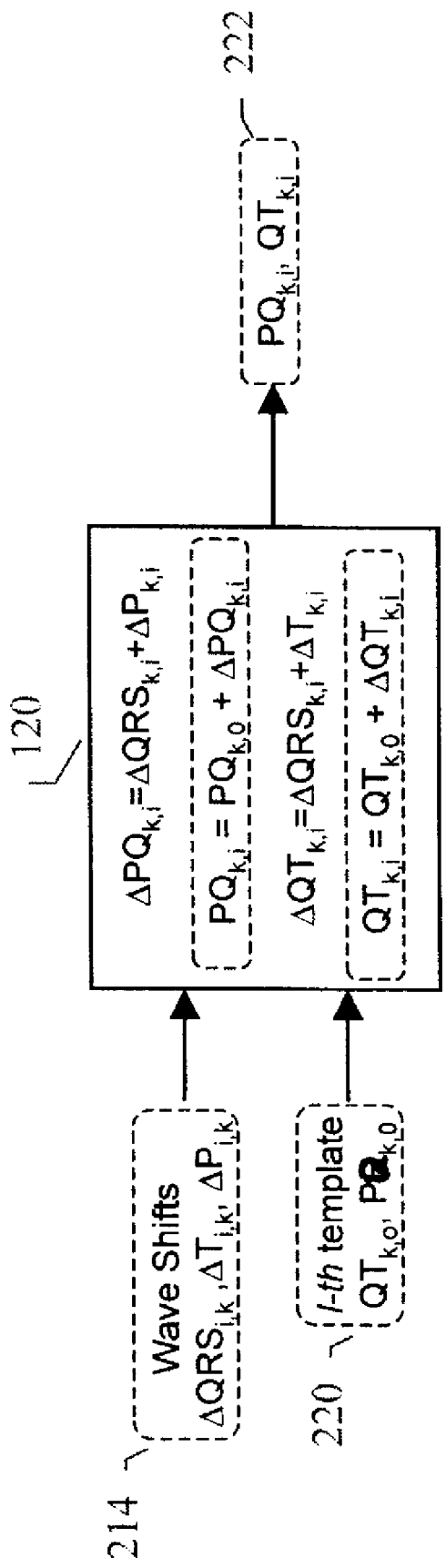
FIG. 12 is a block diagram of a method of construction of ECG intervals for the $k^{th}$ lead.
Figure 13:
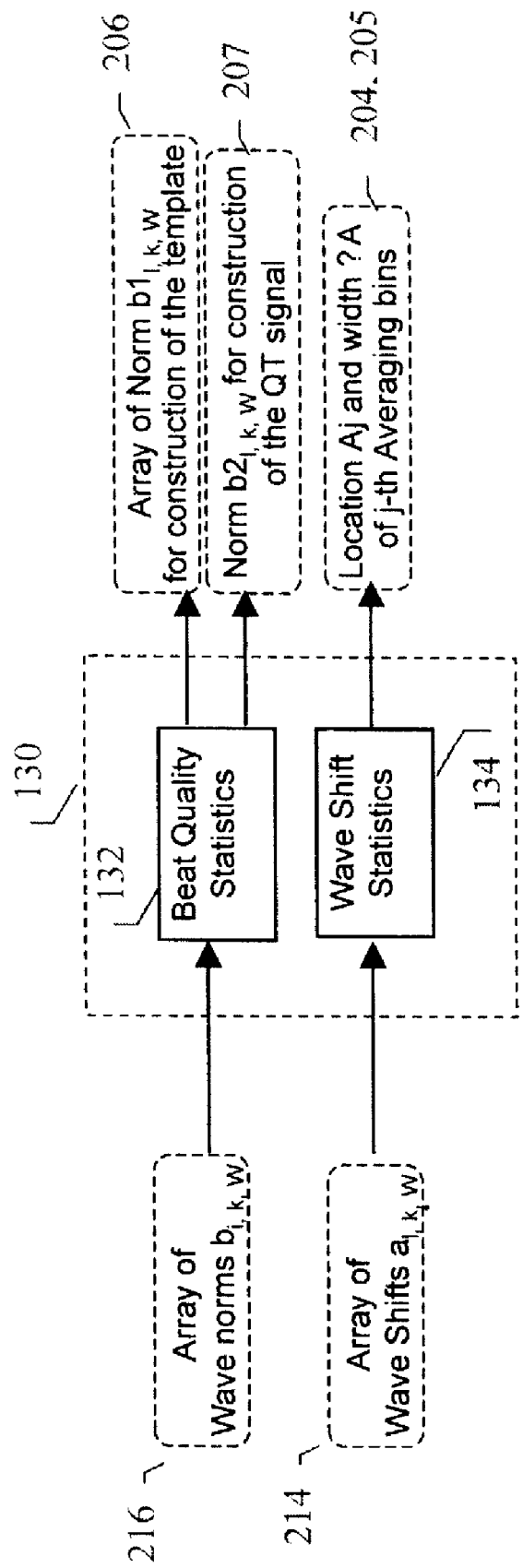
FIG. 13 is a block diagram of a method for the assessment of criteria for the selection of beats for lead k and each of the waves P, QRS, or T.
Figure 14:
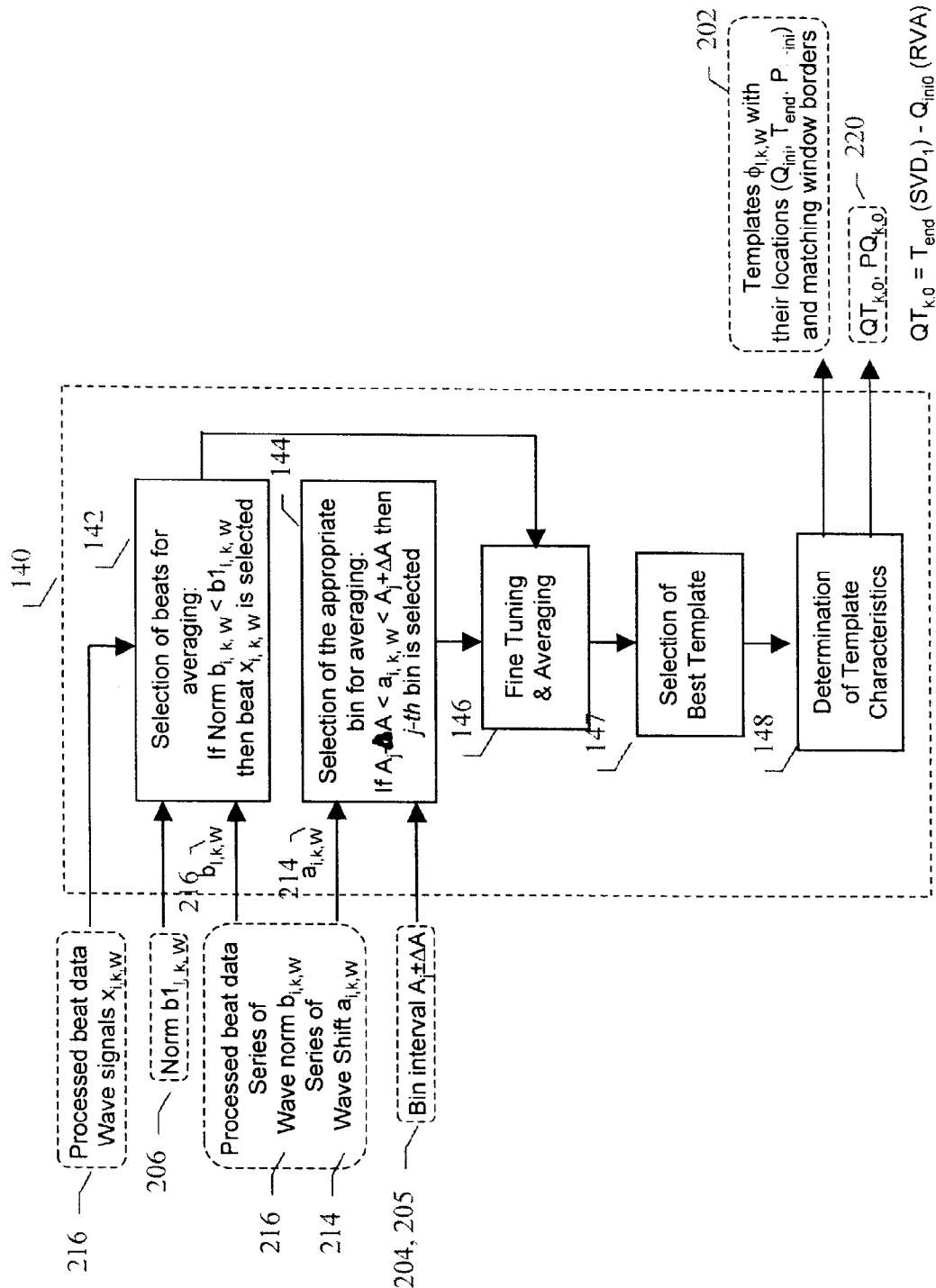
FIG. 14 is a block diagram of a method of construction of the templates for beats $i=N_0(l)$ to $N_1(l)$.

FIG. 14 illustrates further details of step 140 for the construction of templates. As shown in FIG. 14, the construction of templates 140 comprises of five separate steps. In step 142, beats are selected to be used for averaging into any of the averaging bins, whenever the particular norm 216 (b$_{l,k,W}$) is smaller than the norm 216 (b1$_{l,k,W}$) provided by the step beat quality statistics 132 in FIG. 13. If selected for averaging, then in the step 144, the appropriate bin is selected, if the wave shift 214 ($a_{i,k,w}$) fits into the range of the appropriate averaging bin, characterized by the bin interval A±ΔA (items 204 and 205). In the step 146, the wave signal 216 ($x_{i,k,w}$), obtained from the step 110c in FIG. 11, is slightly shifted to be centered in the selected averaging bin. Since there are 7 averaging bins used, the one with the largest number of the accepted beats is accepted as the best template in the step 147. Finally, in the step 148 the template characteristics are determined as described in FIGS. 4-6, to provide the template 202 and the template QT and PQ interval 220.

Initial Beat Selection for Averaging

When analysis begins, templates for the overall ECG signal in each channel are first formed. These initial "global" templates are formed somewhat differently from waveform-specific templates that are formed later. To construct the initial global templates in a presently preferred embodiment, the first 20 beats are collected into a single averaging bin. Then, the mode of the probability function of the RR interval is created for those beats, and its maximum determined. Finally, those ten beats that are closest to the determined maximum are selected, and a template ECG wave for the same beats is then obtained by superimposing the ECG signal based on the fiducial point of the QRS wave.

After the initial global templates have been constructed, breaking points called $PQ_{break}$ (between the P wave and the QRS complex), $QT_{break}$ (between the QRS complex and the T wave), $T_{end}$ (the final point of the T wave) and $P_{ini}$ (the initial point of the P wave) are used to construct individual signal averaged templates for the three principal waveforms QRS, T and P. See FIGS. 3 and 4. Thus, the QRS wave template will ultimately be confined to the time interval between $PQ_{break}$ and $QT_{break}$, the T wave template to the time interval between $QT_{break}$ and $T_{end}$, and the P wave template to the time interval between $P_{ini}$ and $PQ_{break}$. The algorithms that define the breaking points and thus the templates themselves are described separately in greater detail below. Once formed, the QRS, T and P wave templates of the l-th generation are also updated every $M_1(l)$ beats when desired for real-time monitoring.

Even though the waveform is provided by the template, it is necessary to determine characteristic points on the template to measure the intervals and to define the window for comparison of the incoming beat with the template in the next beat selection procedure. These determinations are obtained by fitting a known curve resembling the shape of the template curve to be fitted, but exhibiting well defined deflection points, maxima or minima, since the template curve (such as a T wave) does not necessarily provide them.

To construct the initial global templates, the first (e.g., 20) beats from the electrodes 12 are collected into a single averaging bin, specified as a dedicated register in the computer 16. Then, the mode of a probability function of the RR interval is created for those beats, and its maximum determined. Finally, those ten beats that are closest to the determined maximum are selected, and a template ECG wave for the same beats is then obtained by averaging the superimposed ECG signals based on the fiducial point of the QRS wave.

Global and Regional Properties of the Derived Parameters

This invention employs several measured input ECG signals (multilead signals) and some other derived signals to determine variability of the QT and PQ intervals. Information contained in these signals can be divided into global information and regional deviations from that global information. The most representative 'global signals' are constructed with the singular value decomposition (SVD) method, applied for each of the ECG waves separately.

Decomposed and Reconstructed Signals

The SVD method decomposes the number K of input signals into the number K of orthogonal principal signals ($SVD_n$, n=1 ... K), providing the amplitude ($w_n$) of the decomposed signals (singular values or 'eigenvalues') and the transformation matrix V necessary for the reconstruction of the original signals. The SVD method is based for example on the following theorem of linear algebra (see Press WH. Numerical recipes in C: Cambridge University Press; 1992: 59-70). If A is an M×8 matrix with each column corresponding to one of the 8 standard channels of the 12-lead ECG (I, II, $V_1$, $V_2$, $V_3$, $V_4$, $V_5$, and $V_6$,) and M is the number of samples, A can be written as the product of an M×8 column-orthogonal matrix U, an 8×8 diagonal matrix W with positive or zero elements (the singular values), and the transpose of an 8×8 orthogonal matrix, $$A=U.W.V^T.$$

The matrices U and V are each orthogonal in the sense that their columns are orthonormal, and V is also row-orthonormal, $V \times V^T = 1$.

The above equation can be rewritten to express any matrix $A_{kj}$ as a sum of outer products of columns of U and rows of $V^T$, with the "weighting factors" being the singular values or 'eigenvalues' $w_n$, $$A_{kj} = \sum_{n=1}^{N} w_n U_{jn} V_{kn}, \qquad \text{eq. [x1]}$$

where n, running from 1 to N=8, represents the components of the matrix U or eigenvectors $u_n$ (or principal signals).

In a situation where most of the singular values $w_n$ of a matrix A are relatively very small, A will be well-approximated by only a few terms in the sum [x1], with n running from say, 1 to 3. This means that it is enough to store only a few columns of U and V (the same n ones, say 3) to be able to recover the whole matrix with good accuracy, which reduces the number of multiplications in recovering the matrix and thus also the demand on computer time. SVD is the method of choice for solving most linear least squares problems. Principal signals with the largest amplitudes (the largest eigenvalues) are those represented in the majority of the ECG leads, whereas those with the smallest amplitudes contain local information or are due to noise.

Isotropic Attenuation of Lead Signals

Figure 10:
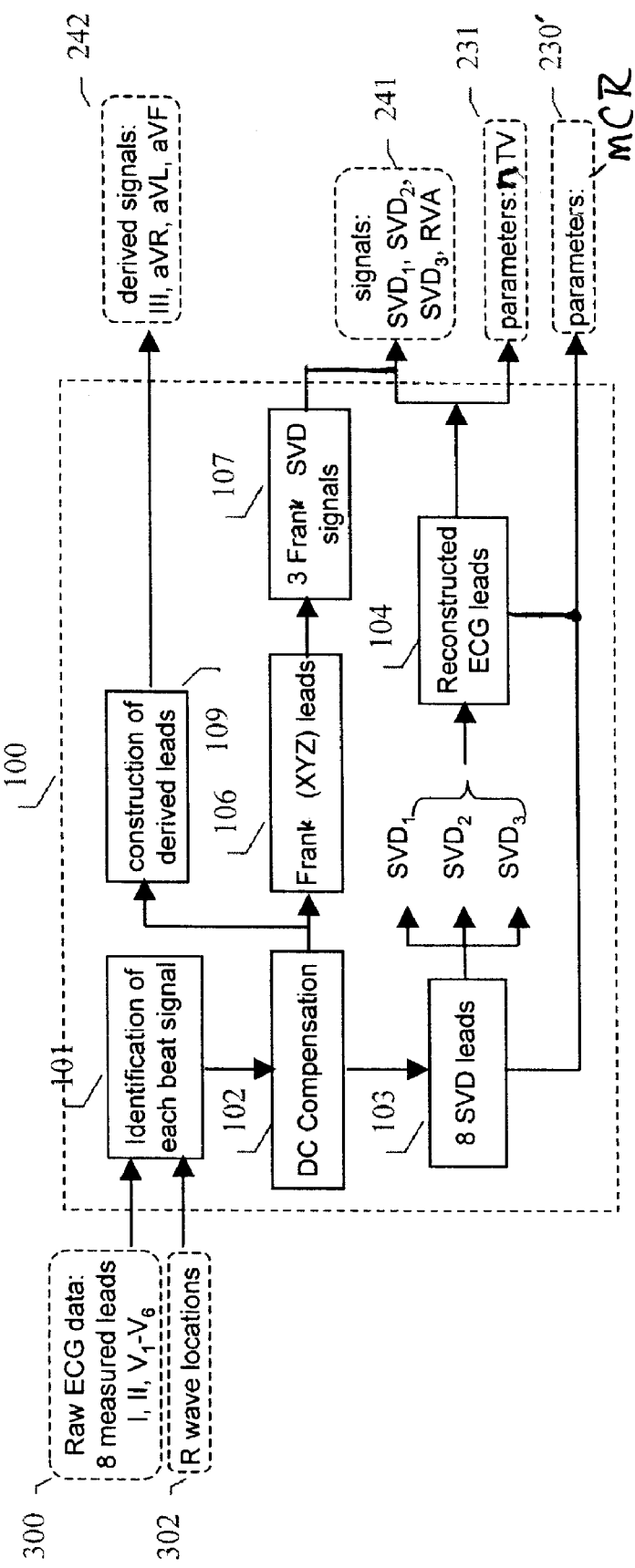
FIG. 10 is a block diagram of a process for the construction of decomposed (SVD) and other derived lead signals and their associated T-wave morphology (TWM) parameters.

The fact that the electrode placement for the standard ECG is predominantly oriented along the ventricular axis also produces a potential limitation. Namely, the first three eigenvalues derived from the standard 8 channels will therefore also represent a somewhat distorted geometrical space that is rather prone to shifting during respiration. To compensate for this distortion and to construct more complete and potentially more stable P, QRS and T wave vectors along the principal axes, the program simultaneously employs a modified SVD algorithm that attenuates each of the measured ECG signals by that amount required to reach the isotropic distribution with respect to the signal's orientation in space. As an approximation of the isotropic distribution, the program employs experimentally derived coefficients for reconstruction of the Frank vector ECG (x, y and z leads) from the standard 12 leads whenever the Frank leads themselves are not being utilized. FIG. 10 depicts this in greater detail.

Specifically, the program uses experimentally verified multiplication factors $a_x$, $a_y$, and $a_z$ of the x, y and z component of the corresponding standard lead to calculate the main diagonal, $d_k$, instead. For the k-th lead, $d_k=\sqrt{(a_x^2+a_y^2+a_z^2)}$. Next, the program multiplies the ECG signal of the k-th lead by $d_k$ and applies it in the SVD algorithm. This in turn allows for the construction of a vector signal from the three largest derived orthogonal components that, in the Frank lead system, would correspond to the radius vector amplitude, or RVA, with time course represented by $RVA(t)=\sqrt{(SVD_1(t)^2+SVD_2(t)^2+SVD_3(t)^2)}$. The RVA signal is then used to construct the so-called $QT_{RVA}$ and $PQ_{RVA}$ signals. Although the RVA signal can only be positive, the $QT_{RVA}$, $PQ_{RVA}$ and other RVA-related intervals are the only intervals derived by the program that theoretically contain the "complete" three-dimensional information as it pertains to the beginning and end of the respective intervals. This overall approach is thus used to: 1) derive principal signals $SVD_1$, $SVD_2$ and RVA for each waveform type; 2) calculate the beat-to-beat QTV and PQV occurring within each of these virtual (decomposed) 'leads' $SVD_1$, $SVD_2$ and RVA (i.e., in addition to within any standard lead); and 3) calculate certain SVD-derived parameters of waveform morphology, including the so-called 'normalized volumes' and 'modified complexity ratios' of the T, QRS and P waves, respectively (described below), as well as the beat-to-beat variability of these morphological parameters.

Reconstruction of the Original Leads

There are two purposes of the reconstruction, to reduce noise and to reduce effects of rotation of the ventricular electrical axis, e.g. due to breathing. The first is accomplished by using only the first three eigenvectors, which contain less local influences such as noise, and the second, by using the transformation matrix for the template instead of the transformation matrix for each particular beat.

The original 8 ECG channels of a standard 12-lead ECG (I, II, $V_1$, $V_2$, $V_3$, $V_4$, $V_5$, and $V_6$) are reconstructed using the first three eigenvectors, namely SVD leads $SVD_1$, $SVD_2$, and $SVD_3$. Thus, the reconstructed ECG leads contain global information incorporated in the main three SVD signals, and are theoretically free of regional information, presented in any particular ECG lead, either due to regional repolarization properties or due to noise. Hence, in the reconstructed ECG signals, noise and regional properties are attenuated by this procedure.

Since the electrical axis is oscillating due to respiration, one can advantageously reconstruct leads from the coordinate system of the ventricles instead of that from the thorax. To do so, one can replace the transformation matrix [eq. x1] of each beat with that of the corresponding template:

$$A_{ikj} = \sum_{n=1}^{3} w_{in} U_{ijn} V_{lkn} \quad \text{eq. [x2]}$$

with index i in $A_{i,k,j}$, $w_{i,n}$ and $U_{i,j,n}$ denoting the particular beat and index l in $V_{l,k,n}$ the transformation matrix of the particular template. Thus, one can partially eliminate the movement artifacts related to respiration that produce rotation of the heart axis, providing a further improvement of the template waveforms. This also allows for a more accurate delineation of parameters of T-wave (or QRS or P-wave) morphology and for a more appropriate rejection of artifactual beats in relation to ongoing TWM, etc.-related statistical analysis.

The above procedure is robust if differences between $V_{l,k,n}$ and $V_{l,k,n}$ are small enough, otherwise problems with instability may occur providing a very distorted reconstructed signal. Empirically, the coefficients associated with large eigenvalues should not differ more than 0.15, and the first three eigenvalues should contain at least 99% of the signal energy. When such conditions are satisfied, as is usually the case, the reconstructed lead signals are similar to the original ones, but with less noise, and exhibit rotations of the ECG vector in space that are typically smaller than 1 degree of angle due to respiration and other factors. When applying the non-oscillating signal of a given ECG lead in the averaging procedure, a 'cleaner' template therefore results that is very appropriate for the determination of parameters of T-wave, P-wave and QRS-wave morphology.

T Wave Morphology and the Reconstructed Leads

Using the T wave as an example, its reconstructed signals contain information about TWM as a global property, whereas deviation of the original ECG signals from the appropriate reconstructed ones describe regional differences.

Global characteristics of TWM can be defined in different ways. For example one can characterize spatial distribution of the T wave by constructing a 3D body with the orthogonal directions along three main 'eigensignals'. It is known that in the normal, healthy heart, 'eigenvalues' decrease very quickly when progressing from the largest eigenvalues to the smallest ones, whereas in the diseased heart they decrease considerably more slowly. If we approximate the 3D body described above as an ellipsoid with axes represented by the main three eigenvalues, it is much more elongated (eccentric) in the healthy heart than in the diseased heart. Elongation can be evaluated as a ratio of the second and the third eigenvalues against the first one, $sqrt(w_2 \cdot w_3)/w_1$. This ratio has a very low value in the case of healthy heart, and increases with the diseased heart, showing an increased spread of the T wave in the space.

The relative T wave residuum (TWR) had been described previously by Malik et al (e.g., U.S. Pat. No. 6,438,409), whereas the 'normalized volume' of the T wave (nTV) and the 'modified complexity ratio' (mCR) of the T-wave are a new and improved parameters of T-wave morphology proposed and utilized herein. Besides the T wave, these improved parameters of morphology can also be applied to the P and QRS waves, or to any portion or combination of the P, QRS and T waves.

Whereas TWR is defined as the sum of squares of the five smallest T-wave eigenvalues, divided by the sum of squares of all eight T-wave eigenvalues (i.e., when utilizing a traditional 8-channel ECG), nTV is defined as the product of the second and the third eigenvalues divided by the first eigenvalue squared, generally expressed as a percent, i.e,. $nTV=100\times[w_2 \cdot w_3/(w_1)^2]$. The meaning of this parameter is the eccentricity of the ellipsoid volume described by the three largest eigenvalues as the ellipsoid axes, since the product of the three largest eigenvalues is proportional to volume, normalized with the largest axis.

The mCR is the ratio of the sum of the squares of the third through the last eigenvalue being considered, to the sum of the squares of all eigenvalues being considered, also expressed as a percent. For example, in the specific case of the 8-channel (12-lead) ECG, $$mCR = 100 \times \sum_{i=3}^{8} w_i^2 \bigg/ \sum_{i=1}^{8} w_i^2$$

where $w_1 \geq w_2 \geq \ldots \geq w_8$. This parameter particularly emphasizes the contribution of the third eigenvalue in the numerator, thus making it distinct from the previously known relative TWR, which instead particularly emphasized the contribution of the fourth eigenvalue in the numerator. The mCR is also distinct from another parameter of T-wave morphology known as the 'complexity ratio' (CR, also known as the 'principal component analysis ratio'), which instead particularly emphasized the contribution of the second eigenvalue in the numerator. As described below, in studies that are being prepared for publication, both the nTV and the mCR have outperformed the relative TWR (and the CR) in distinguishing groups of individuals with cardiomyopathy and/or coronary artery disease from groups of age- and gender-matched healthy control subjects.

In a study being readied for publication that involved: 1) 38 individuals with known cardiomyopathy (CM, cardiac systolic ejection fraction less than 40%); 2) 38 individuals with known coronary artery disease (CAD, $\geq$1 major coronary artery with $\geq$50% stenosis at catheterization) but with normal ejection fraction; and 3) 38 age- and gender-matched healthy control (CNL) subjects, the nTV was the singularly most accurate TWM parameter for correctly identifying the presence of both cardiomyopathy and coronary artery disease [areas under the receiver operating characteristic (ROC) curve of 0.91 and 0.77, respectively]. The performance of the nTV (and of the mCR) was specifically superior to that of the relative TWR and CR, even when the relative TWR and CR were determined along with the nTV and mCR by using appropriate signal averaging for noise reduction rather than just a median beat or a single beat.

It should be noted that the mechanistic rationale for the use of these new parameters of morphology over the prior art is because in nearly all healthy control subjects included in the above study, the most relevant T-wave (and other wave) amplitudes are actually contained not in the first three eigenvectors (or in the "dipolar components", as might be suggested by the prior art of Malik et al), but rather only in the first two eigenvectors. Thus, when disease occurs and the T-wave and other wave eigenvector energies start shifting into more downstream eigenvector components, these new indices of TWM are (thus far) invariably more sensitive than the older indices, which did not focus enough on the third eigenvector. The better performance of these newer (versus the older) parameters of TWM thus suggests that in disease, most of the energies are actually shifting not from eigenvector 3 into the even more downstream eigenvectors, but rather from eigenvector 2 (and/or from eigenvector 1 and 2) into eigenvector 3.

a. QRS Template

Referring again to FIG. 3, the characteristics of the template QRS complex are determined by searching for local minima and maxima as well as by the minimal and maximal time derivative values (slopes) between them (FIG. 11). In a presently preferred embodiment, the initial slope is defined as the first deflection before the fiducial point that is larger than $\frac{1}{10}$ of the maximal slope of the given QRS complex. The crossing of the initial slope with the preceding nearly horizontal segment determines the initial point of the QRS complex, $Q_{ini}$, for each measured ECG lead. Next, the program selects the steepest initial segment of the QRS complex that is larger than 15% of the total QRS signal amplitude, and determines the first and the last point of that segment, $QRS_1$ and $QRS_2$, respectively. These two points are used as a window to determine the $\Delta QRS$, the deviation of the steepest initial segment of the QRS complex of the incoming beat from the same region in the template. This is necessary to correct any QRS shift (jitter) or an improperly detected fiducial point for the incoming signal.

In a presently preferred embodiment, the most reliable $Q_{ini}$ point is considered to be the one derived from a decomposed lead (i.e., specifically, from the RVA signal, discussed above). This $Q_{ini}$ point represents the global beginning of electrical depolarization of the ventricles. It is called $Q_{ini0}$. The final point of the QRS complex, $QRS_{end}$, is determined similarly to $Q_{ini}$, and then the point $QRS_{end0}$ is determined similarly to $Q_{ini0}$. It is $Q_{ini0}$ and $QRS_{end0}$, both obtained from the RVA signal, that in turn determine the breaking points ($PQ_{break}$ and $QT_{break}$) between waves. Specifically, in the presently preferred implementation of the program, $PQ_{break}$ is considered to occur 20 ms before $Q_{ini0}$, and $QT_{break}$ 30 msec after $QRS_{end0}$.

When QTV is determined, the borders for the QRS template ($Q_{ini0}$ and $QRS_{end0}$) as well as the QRS breaking points ($PQ_{break}$ and $QT_{break}$) are treated as the same for all leads. However, new borders and breaking points are computed every time the program (through automatic pre-set at N beats) or the user (through manual interaction) instigates formation of a new template in order to optimally refresh the monitoring going forward.

b. T Wave Template

Referring now to FIG. 4, in the presently preferred embodiment, the onset and offset of the T-wave template are constructed in the following manner. First, a biparabolic curve is constructed consisting of two interconnected parabolic segments, both with an amplitude one half of the total biparabolic curve height, the first part nearer to the QRS complex and the second (distal) part with its apex convex toward the zero line. The first and the last point of the biparabolic curve are designated as $T_1$ and $T_2$, respectively. Both parabolic segments are further divided into three parts, with the apex occurring in the outer third of each parabola. The apex of the distal parabola is later used to estimate the final point of the T wave, $T_{end}$. In addition, in order to more closely replicate the T wave, the horizontal line between points $T_{end}$ and $T_2$ replaces the most distal aspect arising from $T_{end}$. The biparabolic curve is shifted toward the QRS complex, while varying its height and width until finding the best fit to the initial template T wave. Because for waveforms in both the positive and negative directions, several matches might have occurred while approaching from the distal part towards the QRS complex, the one with the largest overall amplitude is selected as the most representative one. The point $T_{end}$ is then determined by the position of the distal apex point. The interval $QT_0 = T_{end} - Q_{ini0}$ is then the estimated absolute duration of the QT interval in that particular ECG lead. In addition to determining $T_{end}$, the program uses both of the extremities of the representative biparabolic curve, $T_1$ and $T_2$, to determine the interval for matching the incoming $T_{end}$ to the $T_{end}$ of the existing template. However, unlike the case for the QRS template borders and breaking points, $T_{end}$ is subsequently treated as unique for each lead. The most representative template QT interval is that obtained using the T wave of the $SVD_1$ lead, $QT_{SVD1, 0}$.

The template QT interval is determined by fitting known parametric non-linear curves to the template waveform constituents. By varying parameters of the chosen curve, it approaches the shape of the given template waveform, and if the selected curve is similar to the shape of the particular wave, then the known characteristic points (the maximum, minimum or any inflexion points) of such a curve define the beginning or the end of the particular wave. Specifically, a biparabolic curve is used to fit the last part of the template T wave and the first part of the P wave, and a multiple straight line curve to fit the complete QRS complex. The template ECG interval is then defined by the most distal points on the two adjacent ECG waves of the template. For the QT interval, it is the initial point on the QRS and the final point on the T wave, and for the PQ interval, the initial point on the P wave and the initial point on the QRS.

However, in case of bad congruency of the biparabolic curve used for fitting with the template waveform, the template QT interval might be inaccurate. When such occurs, it is particularly evident after the reconstruction of templates, manifested in two slightly different QT intervals for the same series of beats, yet made with two different templates. Differences may reach up to 10 ms, which is much greater than those of the ΔQT deviation provided by beat processing, being estimated to be smaller than 1 ms in a good-quality ECG signal.

c. P Wave Template

A procedure similar to that used to form the T-wave template is also used to determine the appropriate borders for a P-wave template in all ECG leads. The method of the present invention later uses the P-wave template and the QRS wave template for determining PQ interval variability (PQV, also known as PR interval variability, PRV), preferably in real time, in a fashion similar to that described for QTV below. Although the focus of the following discussion is, for illustrative purposes, on QTV, the method of the invention is equally applicable to both PQV and QTV, and both QTV and PQV fall within the scope and spirit of the invention.

Algorithm for QTV

In the software program specifically designed for analyses of QTV, the P, QRS and T templates are constructed by signal averaging rather than by using a single beat from the measured ECG signal. In addition, matching of any new incoming complex to the templates in any region of interest is thereafter achieved by shifting of the ECG signal, i.e., not by 'stretching'. It should be understood that the QTV algorithm described herein is principally concerned with quantifying the variability of intervals rather than their absolute values. If for any reason the algorithm chooses a "false" beginning or end point for a given template interval, then all interval values will be biased proportionately, but the beat-to-beat variability in the computed intervals will be unaffected.

In the beat signal matching, i-th beat signal of the k-th lead is first split at the break-points $PQ_{break}$ and $QT_{break}$ into ECG waves $x_{i,k,W}$, with W denoting the particular wave (P, QRS, and T), so that each wave can be manipulated (shifted, normalized) independently of others. Beat waves $x_{i,k,W}$ are thus shifted with respect to the corresponding template wave $\phi_{l,k,W}$ to find the best match at which two parameters are provided, the norm $b_{i,k,W}$, and the delay $a_{i,k,W}$. The norm represents a measure for the quality of matching, i.e. how precisely the beat wave $x_{i,k,W}$ matches the template wave $\phi_{l,k,W}$, and the delay a measure of how much the beat wave has to be shifted to get the optimal match.

Figure 6:
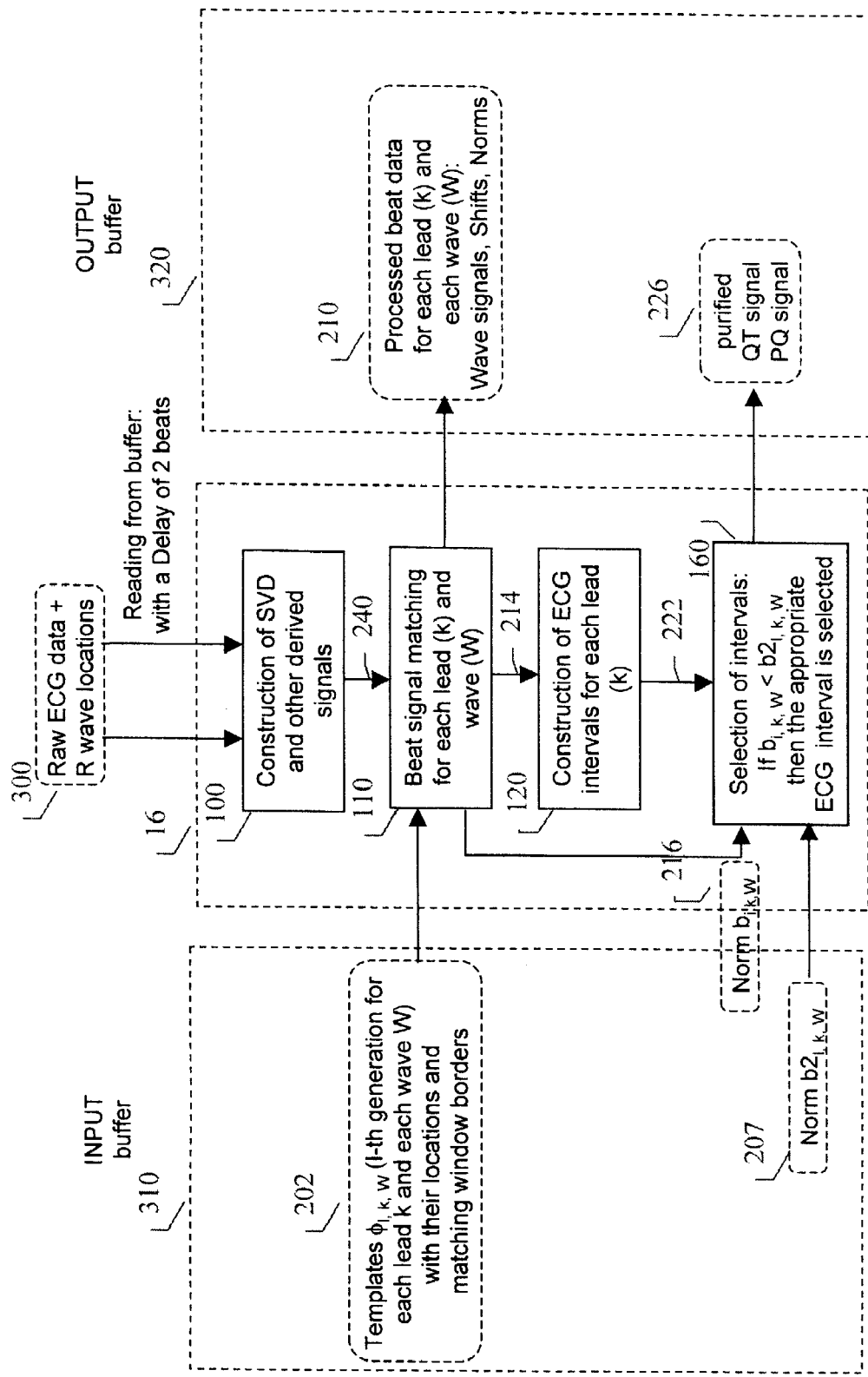
FIG. 6 is a schematic diagram of system for beat signal processing in accordance with this invention.

The beat signal processing is a procedure of matching of ECG waves of each beat with the corresponding template wave that was constructed earlier to get the best match. The procedure for beat signal processing for the QT interval is depicted in FIG. 6. Matching is performed separately for each of the three ECG waves, the waves P, QRS and T, respectively. The purpose of matching is to reach an optimal alignment of each beat component (waves P, QRS and T) with the respective template wave and to check for similarity with the appropriate template wave that was constructed previously, thus providing two matching parameters, the time shift and the norm, respectively.

The time-shift or the delay measures how much a particular wave has to be shifted with the respect to the template to get the optimal match, whereas the norm is a measure of quality of the measured wave and provides information about how accurately that particular wave matches the appropriate wave of the present or former template. The processed beat signal with shifted waves, the corresponding time-shifts and norms are saved into a buffer memory to be used in the next construction of templates. The time shift and properties of the templates are used to construct beat by beat ECG intervals, such as QT or PQ interval. Finally, the statistical distribution of wave norms and delays is applied to provide an acceptable QT (and PQ) signal and other beat-related parameters.

As shown in FIG. 6, an input buffer 310 retains the templates 202, as well as the Norm $b2_{i,k,W}$ 207. These data are provided to the computer 16 for the processing of raw ECG data in digital form from the PC ECG console (see FIG. 2). The beat signal processing 60a and 60b (see also FIG. 7) comprises four separate steps. Step 100 involves the construction of decomposed (SVD) and other derived ECG signals, shown in greater detail in FIG. 10; step 110 involves beat signal matching for all leads k; step 120 provides the construction of ECG intervals (the QT interval, the PQ interval); and step 160 provides the selection of those QT intervals (removal of artifacts) to get a purified QT signal 226, which is sent to an output buffer 320 and is used in the further analysis, as described below. The output buffer 320 also retains a copy of the processed beat data 210 for each lead and each wave.

As shown in FIG. 10, the buffer 300 with Raw ECG data and buffer 302 with R wave locations is provided to Step 100 for processing. In step 101, each beat signal is identified, and provided to step 102 for DC compensation. The compensated signal is utilized in deriving all relevant eigenvector (SVD) leads (e.g., 8), of which the first three also go to block 104 for the 'reconstruction' of the ECG leads and thus contribute to the SVD output in block 241. DC compensation is also provided to the derived Frank leads in block 106 and toward the construction of the other derived leads in block 109. These latter signals are output to buffer 242 as derived signals. The derived Frank lead signals in 106 are subjected to SVD and transformed into Frank SVD signals in block 107, which in turn contributes to the outputted SVD signals such as the RVA in block 241. Finally, the SVD leads from block 102 and reconstructed ECG leads from block 104 provide signals for the parameters nTV and mCR in blocks 231 and 230'.

As shown in FIG. 11, in the first sub-step 110a of step 110, a broader time interval containing the complete wave component is used to reach the best fit in the complete wave matching step 114. Specifically, the points $QT_{break}$ and $T_2$ are used for the T wave, $PQ_{break}$ and $QT_{break}$ for the QRS complex, and $P_1$ and $PQ_{break}$ for the P wave. In this sub-step, each raw wave $x_{i,k,W}$ of any incoming beat is, first, shifted in the step 112 by a certain amount (time shift 119) to or from the trigger point, and then the amplitude of the incoming wave component is normalized in the step 113 with respect to the template to get a normalized shifted (NS) wave 116, i.e., the raw wave 211 is adjusted to reach the same amplitude (or alternatively the same surface area under the curve) in the same time interval as that of the template (FIG. 5a).

The quality of matching with the template obtained in the step 114 in the appropriate time window is evaluated by an error signal 115 as a function of time shifting $\epsilon_{i,k,W}(a_{i,k,W})$. Error is defined as the sum of the squared differences between the template wave $\phi_{i,k,W}$ (W denoting waves P, QRS or T) and the NS wave 116, i.e., the shifted version of the incoming wave $x_{i,k,W}$ of beat i and of lead k and W-th wave $\epsilon_{i,k,W}$ $$\varepsilon_{i,k,W}(a_{i,k,W}) = \sum_{j=n_1(W)}^{n_2(W)} [\varphi_{l,k,W}(T_\phi + j) - x_{i,k,W}(T_x + a_{i,k,W} + j)]^2,$$

where $a_{i,k,W}$ is the time-shifting parameter of ECG lead k, $T_\phi$ and $T_x$ are the triggering point of the template and of the beat i, respectively, and $n_1(W)$ and $n_1(k,W)$ are the beginning and the end of the matching windows, e.g., $QT_{break}$ and $T_2$ in the first matching and $T_1$ and $T_2$ in the second matching, respectively, in the case of the T interval. The time shift $a_{i,k,W}$ is varying in the step 111a until finding the smallest error. Since the matching interval on the beat waveform changes with shifting, normalization has to be performed after each change of time shift. The sub-step 110a is important for providing the "norm" 216, the index of the quality of matching that is mathematically defined below.

In the second sub-step 110b, further shifting of the NS wave 116 by varying time shift $a_{i,k,W}$ with the initial value 119 in the step 111b is further performed to achieve the best fit in a smaller time window in the step 118. Specifically, the points $T_1$ and $T_2$ define the best fit for the end of the T wave (FIG. 5b), the points $QRS_1$ and $QRS_2$ the best fit for the beginning the QRS complex, and the points $P_1$ and $P_2$ the best fit for the beginning of the P wave. The parameter $a_{i,k,W}$ is changed for that beat in the step 111b to find that particular value $a_{i,k,W}$ 214, which occurs at the minimal $\epsilon_{i,k,W}(a_{i,k,W})$, until the step of $a_{i,k,W}$ is <0.1 ms. To achieve shifting of the P, QRS and T waves by a noninteger value of a, interpolation of the waves between the measured sampled values is necessary.

To obtain the processed wave signal that enters the averaging procedure, a third step 110c is performed in which the appropriate raw wave 211 is shifted in the step 11B by an amount 11A, determined by an appropriate SVD signal: for the T and P wave it is usually the $SVD_1$ signal for all leads, and for the QRS wave it is usually the RVA signal.

The value of $\epsilon_i(a_k)$ after the first matching represents the quality of matching, or the norm. The norm is mathematically a dimensionless quantity that represents the average deviation of the incoming wave from the template, divided by the amplitude (A) of the wave in that interval, i.e., $$Normb_{i,k,W} = \frac{\sqrt{\epsilon_i(a_{i,k,W})/(n_2(W) - n_1(W) + 1)}}{A}$$

The lower the norm, the better the fit, and when the incoming wave and the template are perfectly matched, the norm=0.

Two Dimensional Matching of Beats with the Template

In order to construct decomposed signals using templates, obtained by a synchronized superposition of beats into a certain averaging bin, it is necessary that these templates had to be constructed using the same series of beats for all relevant leads and that the fine tuning to achieve a synchronized superposition had to be the same for the particular beat in all leads. Hence, beat (or wave) selection for construction of the template and its time-shifting for a synchronized superposition should be controlled by the norm and the delay from a single lead for all leads. One way to achieve it is to use a signal with the most prominent wave, such as is the $SVD_1$ signal. A reasonable approach is to use the $SVD_1$ signal and its norm and delay to control averaging of the T wave and P wave in all leads, and the RVA signal to control averaging of the QRS, since sometimes the initial electrical activity in the QRS complex appears earlier in $SVD_2$ than in $SVD_1$.

Since the first two SVD signals generally carry more than 99% of energy in the normal heart and more than 90% of the energy in the diseased heart, they are good representatives for the global description of electric phenomena of the heart, much better than any single SVD signal. For this purpose signal matching in a preferred embodiment is performed in two dimensions of the $SVD_1$-$SVD_2$ planes, to calculate the area of the loop described by each ECG wave and match the loop of the single beat signal with that of the template signal. The error signal and the norm are calculated similarly to that of a single lead, except that a difference between the area described by the beat signal and the area described by the template signal is used when increasing the sample number and integrated from the beginning to the end of the particular wave. Since it is lead independent, index 0 is used for the lead, and the error signal is then equal to $$\epsilon_{i,0,W}(a_{i,0,W}) = \sum_{j=n_1(W)}^{n_2(W)} [\varphi_1 - x_1]^2 + [\varphi_2 - x_2]^2$$

where the template and signal samples are first extrapolated to get the middle position $j+\frac{1}{2}$ between the samples j and j+1, $$\phi_1 = \phi_{I,SVD_1,W}(T_\phi + j),$$

$$\phi_2 = \phi_{I,SVD_2,W}(T_\phi + j)$$

$$x_1 = x_{i,SVD_1,W}(T_\phi + j + a_{i,0,W}),$$

$$x_2 = x_{i,SVD_2,W}(T_\phi + j + a_{i,0,W})$$

The error signal is finally normalized to the combined amplitude of both $SVD_1$ and $SVD_2$ signals, $$A_{I,0,W} = \sqrt{A_{SVD_1}^2 + A_{SVD_2}^2}$$

The corresponding norm $b_{i,0,W}$ for the wave W and beat i is $$Normb_{i,k,W} = \frac{\sqrt{\epsilon_{i,0,W}(a_{i,0,W})/(n_2(W) - n_1(W) + 1)}}{A_{I,0,W}}$$

Construction of ECG Intervals (the QT Interval, the PQ Interval)

The QT interval is assessed in two steps, first, by determining the template QT interval, i.e., the QT interval of the template beat, and second, by determining beat QT deviation, $\Delta QT$, i.e., how much a particular wave of the particular beat is delayed with respect to the template one.

Each template $\phi_{I,k,W}$ when constructed, provides its waveform that is used for matching with a particular beat wave, its location with respect to the fiducial point on the QRS complex and the width, that serves as a window for matching. The absolute value of QT interval $QT_{k,0}$ is usually obtained as a distance from the initial point $Q_{ini0}$ of the QRS complex of the RVA signal and the final point $T_{end}$ on the T wave of the $SVD_1$ signal.

It is expected that QT intervals differ among different leads. Hence, the $QT_{i,k}$ interval of i-th incoming beat and of k-th ECG lead differs from the template $QT_{k,0}$ by an amount $QT_{i,k}$:

$$QT_{i,k} = QT_{k,0} + \Delta QRS_i + \Delta T_{i,k}$$

where $\Delta T_{i,k}$ is the interval obtained by shifting the $T_1$-$T_2$ segment of the i-th T wave to match the template, and $\Delta QRS_i$ by shifting the $QRS_1$-$QRS_2$ segment of the QRS complex, respectively.

In detail, the sum of time displacement of the T ($\Delta T_{i,k}$) and QRS waves ($\Delta QRS_i$) forms the QT interval change for the i-th beat and the k-th ECG lead ($\Delta QT_{i,k}$), and is calculated according to the equation:

$$\Delta QT_{i,k} = \Delta T_{i,k} + \Delta QRS_i$$

where $$\Delta T_{i,k} = \hat{a}_{i,k(T)} \Delta t, \text{ and } \Delta QRS_i = \hat{a}_{i(QRS)} \Delta t$$

and where $\hat{a}_{i,k(T)}$ and $\hat{a}_{i(QRS)}$ represent the time-shifting factors of the T and QRS wave matching windows and $\Delta t$ the digitalization interval (e.g., 1 ms). Because $Q_{ini0}$ (and $QRS_{end0}$) is the same for all leads, this same procedure also applies to $\Delta QRS_i$. In a 12-lead ECG, the latter is selected among all eight measured ECG channels as that $\Delta QRS_{k,i}$ which is placed to the time instant of the highest density of the $\Delta QRS_{k,i}$ distribution, using a technique similar to that described for selection of the initial 20 beats with respect to the RR interval. Such $\Delta QRS_i$ typically differ less than 0.3 ms from a corresponding $\Delta QRS$ change obtained from the derived vector ECG using derivation methods available in the public domain.

Finally, the QT interval for the i-th beat is calculated according to the equation:

$$QT_{i,k} = QT_{k,0} + \Delta QT_{i,k}$$

where $QT_{k,0}$ is the duration of the template QT interval in the k-th lead.

The algorithm thus provides the QT interval for each beat such that the T wave and QRS complex best match the template T wave and QRS complex under the time-shift model. Similar algorithms are also used for the assessment of PQV.

Most decomposed signals obtained by the SVD method are thereinafter not further used since they are inferior to the SVD signals obtained by averaging the particular SVD lead beats. However, the eigenvalues themselves are useful to determine parameters such as the 'normalized volume' and mCR of the template T-wave (and of the template P and QRS waves), and also the variability of these parameters from beat-to-beat.

The QT interval of the particular beat is obtained when the QT deviation of the particular beat from the corresponding template in the region of that characteristic point is added to the template QT interval, $QT = QT_{template} + \Delta Q + \Delta T$.

The particular ECG interval of the i-th beat is obtained by summation of the corresponding template ECG interval and wave delays of the beat. Specifically, the QT interval of the k-th lead is equal to the sum of the template's $QT_{k,0}$ and $a_{i,k,QRS}$ and $a_{i,k,T}$ ($a_{i,k,QRS} = \Delta QRS_{i,RVA}$ and $a_{i,k,T} = \Delta T_{i,k}$).

Finally, a purified QT interval signal (and PQ interval signal) is obtained by eliminating the 'bad' QT (and/or PQ) intervals (e.g., due to artifacts not belonging to the same cluster). The i-th beat QT interval is selected if the norm $b_{i,k,W}$ of the T wave and that of the QRS complex were both smaller than the corresponding norm $b2_{i,k,W}$, which was determined in the assessment of criteria for selection of beats before constructing the template. The purified QT signal (and/or PQ signal) is used for further statistical analysis.

Selection of Beats for the Construction of Templates

During construction of the template, the norm in each particular ECG lead is treated statistically to obtain the mean±SD norm value in that lead. In a preferred embodiment, the match between the incoming wave and the template is considered acceptable if the norm of any beat is within one SD of the mean norm in the corresponding ECG lead. This procedure helps in providing an acceptable number of beats for averaging even in case of noisy signals. For the QRS and T waves, an acceptable norm is usually less than approximately 0.15.

As shown in FIG. 13, the assessment of criteria for selection of beats 130 is comprised of two steps, the step beat quality statistics 132, and the step wave shift statistics 134. The step 132 provides two series of norms, the norm 206 ($b1_{i,k,W}$) for selection of beats 142 for construction of the particular template, and the norm 207 ($b2_{i,k,W}$) for selection of beats 92 of the QTV statistics 90 for obtaining the purified QT signal 212, free of 'bad' QT intervals. The step 134 provides the location 204 and width of averaging bins ($A_{k,W}$ and $\Delta A_{k,W}$, respectively), used in the step 144 of FIG. 14 for selection of the appropriate bins for averaging.

Figure 9:
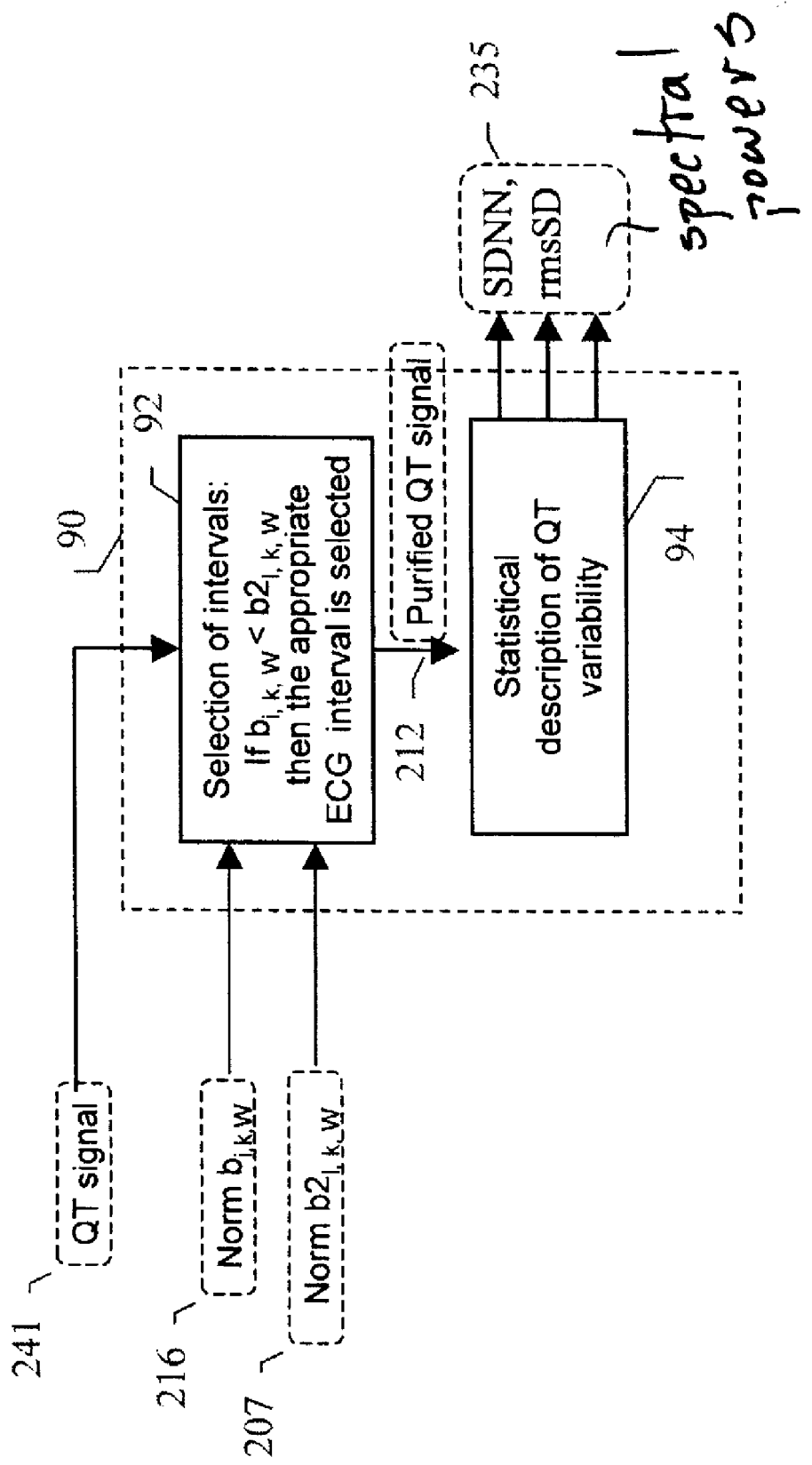
FIG. 9 is a block diagram of a process of developing QTV statistics and the decomposition of the QT signal into components.

The QTV statistics are determined as shown in FIG. 9. The QT signals 241, and the norm values 216 and 207, are input to the processor for this determination in step 90. In step 92, if b is less than b2, then the appropriate ECG interval has been selected, and the purified QT signal is sent to step 94, for the statistical description of QTV. Typical statistical descriptions of time and frequency domain variability such as the standard deviation of normal-to-normal QT intervals (SDNN QT), the root mean square of the successive QT interval differences (rMSSD QT), the spectral powers of QTV, etc. are then output to the buffer 235.

After collecting a predefined number of beats (say $M_1(1)$), the following steps are applied in a presently preferred embodiment:

1. Beat quality statistics provides the wave norm distribution for each ECG lead to determine:
   a. Norm b1 ($b1_{i,k,W}$), a minimal quality of matching that is required to select beats for the construction of the template. Norm b1 represents that value in the norm frequency distribution that occurs either 2 SD (standard deviations) after the single peak in the distribution or in case the distribution has two peaks, in the trough after the first peak if the area under it is larger than 30%. In the case of the T wave or P wave, the norm distribution of the $SVD_1$ signal is used, whereas in the case of the QRS complex, the RVA signal is used instead of the $SVD_1$ signal;
   b. Norm b2 ($b2_{i,k,W}$), a minimal quality of matching that is required for accepting the beat for statistical description. Norm b2 is defined by the Mean Norm±6 SD+0.05. This assures rejection of bad waves, but provides a reasonable number of beats for the description, particularly for any desired later comparison of QT or PR interval variability with RR interval variability.
2. Wave delay statistics are obtained for determination of the averaging bin characteristics. This provides the distribution of wave delays ($\Delta T$, or $\Delta P$) of the $SVD_1$ signal to determine the position and the width of each averaging bin (also for all other ECG leads). Seven bins are determined so that they cover the interval of wave delays ($\Delta QRS$, $\Delta T$, or $\Delta P$) of Mean delay±3.5 SD, so that the position and the width of the central bin is Mean delay±0.5 SD, and 3 bins are positioned left and 3 to the right of it displaced by 1 SD. In the case of $\Delta QRS$ wave delay, the RVA signal is used instead of the $SVD_1$ signal.
3. Selection of a particular beat for the construction of the T or P wave template is based on comparison of the Norm of the beat $SVD_1$ signal with respect to the Norm1 of the template $SVD_1$ signal (from the previous SVD procedure): if a norm of the particular wave (T or P) of the $SVD_1$ signal is smaller than Norm1 of the $SVD_1$ template, then the beat is accepted for the continued construction of the template for all ECG signals (ECG leads I, II, and V1 ... V6) [Para 28]. Construction of the QRS wave is, however, based on the norm $b_{i,RVA,W}$ of the RVA signal.
4. Selection of the corresponding bin for averaging. For each ECG lead, averaging=superposition of the selected beats into the corresponding averaging bin, which is determined by the delay of the corresponding wave (T, and P) of the $SVD_1$ signal, i.e., the selection of the averaging bin is controlled by the $SVD_1$ signal. Again, in case of the QRS wave, the RVA signal is used instead of SVD$_1$ signal. Selection of SVD$_1$ or RVA signals to drive selection of averaging bins assures that such averaging occurs synchronously in all leads, necessary to obtain the lead templates for construction of the SVD signals.

Instead of using a single bin for the signal averaging of any particular ECG waveform, the program uses seven bins that cover the expected variability interval of each waveform type. An averaging bin is a buffer into which beat waveforms $x_{i,k,W}$ are superimposed for the purpose of averaging if the delay $a_{i,k,W}$ that had been obtained by processing of i-th beat falls into a certain range. For each wave W and each lead k 7 averaging bins are used with the index J running from −3 to 3, each having the width of $\Delta A_{k,W}$, so that all of the 7 bins cover the interval of delays of $A_{k,W} \pm 6$ SD given by the statistical distribution of $a_{i,k,W}$ of beats of the l-th generation, where $A_{k,W}$ is the mean value and SD the standard deviation of that particular distribution. (Hence, $\Delta A_{k,W}=2*6/7$ SD). In order to be accepted for averaging into a certain bin, the time-shift $a_{i,k,W}$ has to be the value of $A_{k,W}+(J\pm\frac{1}{2})*\Delta A_{k,W}$.

Hence, for QTV, the first bin is used for averaging of the shortest QT intervals, and the successive bins for averaging of successively longer QT intervals. The variability interval is defined from the variability record during previous construction of the template, and is initially set to 15 ms. Thus, for example, if the T wave variability interval in lead II was 14 ms during template construction, then each bin for averaging will be 2 ms wide. Before adding the wave into the corresponding bin for signal averaging, the wave is appropriately shifted to adjust for jitter in that particular bin. This creation of several bins for signal averaging helps to prevent an over-reliance on initial values. At least seven templates are therefore constructed for each waveform in each ECG lead, and the bin with the highest number of accepted beats is the one ultimately selected to provide the template. The norm is therefore not the only criterion controlling the averaging procedure, and the final percentage of beats that ultimately constitute a template is typically between 35 and 50%. Despite the potential for a reduction in the number of beats, the quality of the template is nevertheless improved due to selection of the most similar beats.

Beat Selection for Construction of the Purified QT Signal

A series of the QT interval presents the QT signal, which is further employed to describe the statistical properties or QT variability. Also, the series of the particular norm represents the norm signal providing information on which beats are appropriate for construction of the next template and/or for inclusion in the statistical analysis. A large norm value may mean that the ECG beat waveform is contaminated with noise or that the particular wave is very different from most others. In both cases, the beat should not be incorporated into the QTV statistical analyses. On the other hand, large changes in the norm signal may predict cardiac abnormality, such as is the case with T wave alternans.

Time Series Analysis

The program uses the QTV (and corresponding PQV) algorithm as described above to generate, in real time or offline, the time series of the QT and PQ intervals along with that of the RR interval. Such time series are analyzed and their results displayed and updated using standard indices of time and frequency domain variability such as the SDNN QT (and SDNN PQ and SDNN RR), the rMSSD QT (and rMSSD PQ and rMSSD RR), spectral powers, etc., as noted above. In addition, the beat-to-beat variability of the parameters of morphology of the T, P, and QRS waves (e.g., of the nTV and mCR of TWM) is similarly analyzed, displayed and updated, in real time as desired, as are changes in indices that attempt to "correct" QTV, PQV and waveform morphologic variability for simultaneous variability in RR intervals.

To this point, the present invention has been described as based on a computer, whether used in real time or to store data in a data base for later analysis. However, the present invention may also have application to other devices, such as for example implantable devices such as pacemakers, cardioverters, defibrillators, heart monitors, heart synchronizers and drug dispensing pumps, wherein the device is preferably able to trigger a warning signal when the calculated characteristic of cardiac electrical operation is outside of certain predetermined limits. Further, the output signal developed by the device may be used for monitoring the condition of the patient's heart; monitoring the progression of disease in the patient's heart; controlling the rhythm of the patient's heart; raising an alarm when predetermined limits are exceeded; and/or controlling a drug dispensing pump.

The principals, preferred embodiment, and mode of operation of the present invention have been described in the foregoing specification. This invention is not to be construed as limited to the particular forms disclosed, since these are regarded as illustrative rather than restrictive. Moreover, variations and changes may be made by those skilled in the art without departing from the spirit of the invention.

I claim:

1. A method for analyzing electrocardiograph signals from a plurality of ECG leads comprising the steps of:
    sensing analog fluctuations in voltage simultaneously from the plurality of ECG leads, the fluctuations in voltage resulting from electrical activity of a heart and defining a plurality of analog signals;
    converting such signals having an analog value to digital values corresponding substantially to the analog value of the signals;
    analyzing the digital values of the record in real-time by:
        identifying a time of each R wave of a heartbeat;
        defining individual signal averaged templates for the T wave and the QRS wave for a series of heartbeats by segmenting each heartbeat of the series of heartbeats at:
            i. the beginning and the end of the QRS wave; and
            ii. the beginning and the end of the T wave;
    utilizing the defined individual templates to determine alteration values for individual T waves and QRS waves of an individual heartbeat, the alteration values comprising shifts in time of the T wave and QRS wave as error functions for the heartbeat; and
    assessing changes in QT interval for each heartbeat using the T wave template, the QRS wave template, and the series of heartbeats to determine beat-to-beat variability of the QT intervals of the heartbeats.

2. The method of claim 1 further comprising the step of recording the digital values in a record before the step of analyzing the digital values of the record.

3. The method of claim 1, further comprising the step of constructing a singular value decomposition from at least two converted digital values.

4. The method of claim 1, further comprising the steps of:
    iteratively refining the template by adjusting the template based on a plurality of more recently received beat data and;
    iteratively assessing the time variation of each beat as it is received to the iteratively refined template.

5. The method of claim 1, further comprising the steps of defining a norm for each wave as an estimate of the noise of matching for each wave of a selected beat; and selecting only selected ones of the beats for averaging on the basis of the similarity in the QT signal value and of the beat quality as assessed by the norm.

6. A system for analyzing electrocardiograph signals from a plurality of ECG leads comprising:
   means for sensing analog fluctuations in voltage simultaneously from the plurality of ECG leads, the fluctuations in voltage resulting from electrical activity of a heart and defining a plurality of analog signals;
   means for converting such signals having an analog value to digital values corresponding substantially to the analog value of the signals;
   means for analyzing the digital values of the record in real-time by:
   identifying a time of each R wave of a heartbeat;
   defining individual signal averaged templates for the T wave and the QRS wave for a series of heartbeats by segmenting each heartbeat of the series of heartbeats at:
   i. the beginning and the end of the QRS wave; and
   ii. the beginning and the end of the T wave;
   means for utilizing the defined individual templates to determine alteration values for individual T waves and QRS waves of an individual heartbeat, the alteration values comprising shifts in time of the T wave and QRS wave as error functions for the heartbeat; and
   means for assessing changes in QT interval for each heartbeat using the T wave template, the QRS wave template, and the series of heartbeats to determine beat-to-beat variability of the QT intervals of the heartbeats.

7. The system of claim 6, wherein the system is included in an implantable device.

8. The system of claim 6, wherein the means for assessing changes in QT interval develops an output signal that is provided to one of a group consisting of means for monitoring the condition of the patient's heart; means for monitoring the progression of disease in the patient's heart; means for controlling the rhythm of the patient's heart; means for raising an alarm when predetermined limits are exceeded; and means for controlling a drug dispensing pump.

* * * * *